(12) United States Patent
Sherman

(10) Patent No.: US 8,856,968 B2
(45) Date of Patent: Oct. 14, 2014

(54) FOOT STABILIZER SOCKS AND STABILIZER PADS THEREFOR

(75) Inventor: Daryl C. Sherman, Waterloo (CA)

(73) Assignee: PTX Performance Products, Inc. (CA)

( * ) Notice: Subject to any disclaimer, the term of this patent is extended or adjusted under 35 U.S.C. 154(b) by 492 days.

(21) Appl. No.: 12/878,996

(22) Filed: Sep. 9, 2010

(65) Prior Publication Data

US 2011/0119808 A1    May 26, 2011

Related U.S. Application Data

(60) Provisional application No. 61/264,621, filed on Nov. 25, 2009.

(51) Int. Cl.
*A43B 17/00* (2006.01)
*A61F 5/01* (2006.01)

(52) U.S. Cl.
CPC ................ *A61F 5/0111* (2013.01)
USPC ................................. 2/239; 2/241

(58) Field of Classification Search
USPC ............ 2/239, 241, 409, 267; 36/71, 89, 92; 128/893, 894, 882; 602/65
See application file for complete search history.

(56) References Cited

U.S. PATENT DOCUMENTS

| | | | |
|---|---|---|---|
| 2,638,601 A | | 5/1953 | Bullard, III |
| 2,790,975 A | * | 5/1957 | McCormick ...................... 2/239 |
| 3,925,916 A | * | 12/1975 | Garbuio ............. 36/71 |
| 4,005,494 A | * | 2/1977 | Burn ................................. 2/239 |
| 4,445,233 A | * | 5/1984 | Rubin ............................. 2/239 |
| 4,726,126 A | * | 2/1988 | Bernhard ......................... 36/89 |
| 4,811,727 A | * | 3/1989 | Etienne ............................ 602/23 |
| 5,092,347 A | * | 3/1992 | Shaffer et al. ................. 128/892 |
| 5,185,000 A | * | 2/1993 | Brandt et al. ................... 602/63 |
| 5,199,941 A | * | 4/1993 | Makinen ......................... 602/27 |
| 5,230,333 A | * | 7/1993 | Yates et al. .................... 607/111 |
| 5,329,640 A | | 7/1994 | Hourigan |
| 5,625,904 A | * | 5/1997 | Kline ................................ 2/239 |
| 5,791,163 A | | 8/1998 | Throneburg |
| 5,898,948 A | | 5/1999 | Kelly et al. |
| 6,021,527 A | | 2/2000 | Lessard |
| 6,138,281 A | | 10/2000 | Chiaruttini |
| 6,234,988 B1 | | 5/2001 | Brother et al. |
| 6,275,997 B1 | | 8/2001 | Richardson |
| 6,401,256 B1 | | 6/2002 | Shreve |
| 6,446,267 B1 | | 9/2002 | Shah |
| 6,474,006 B1 | * | 11/2002 | Cummings et al. ............. 36/142 |
| 6,564,392 B1 | | 5/2003 | Buckwald |
| 6,629,945 B1 | * | 10/2003 | Stromgren ..................... 602/65 |

(Continued)

*Primary Examiner* — Khoa Huynh
*Assistant Examiner* — Andrew W Collins
(74) *Attorney, Agent, or Firm* — Steven M. Greenberg; CRGO Law

(57) ABSTRACT

A stabilizing sock has a foot section having a shape corresponding to a human foot and comprising a rearfoot portion corresponding to human calcaneous and talus bones and to tibial and fibular malleoli, a forefoot portion corresponding to human metatarsal and phalanx bones, and a midfoot portion between the rearfoot portion and the forefoot portion and corresponding to human cuboid, navicular and cuneiform bones. The sock has a medial stabilizer region on a medial side of the sock and a lateral stabilizer region on a lateral side of the sock. The medial stabilizer region covers a forward medial region of the rearfoot portion and a rearward medial region of the midfoot portion, and the lateral stabilizer region covers a forward lateral region of the rearfoot portion. The sock may also include lace bite protector regions and boot bang protector regions. Kits for assembling stabilizing socks are also described.

4 Claims, 43 Drawing Sheets

(56) References Cited

U.S. PATENT DOCUMENTS

| | | | |
|---|---|---|---|
| 6,729,164 B2* | 5/2004 | Shibata | 66/178 R |
| 7,140,128 B2* | 11/2006 | Huckle | 36/54 |
| 7,346,936 B2 | 3/2008 | Vargas et al. | |
| 2002/0083622 A1* | 7/2002 | Joubert et al. | 36/117.6 |
| 2004/0049951 A1* | 3/2004 | Chen | 36/93 |
| 2005/0076421 A1 | 4/2005 | Littzi | |
| 2006/0026740 A1 | 2/2006 | Vargas et al. | |
| 2006/0195971 A1 | 9/2006 | Lambertz | |
| 2007/0022519 A1 | 2/2007 | South | |
| 2007/0033710 A1 | 2/2007 | Lambertz | |
| 2007/0074334 A1 | 4/2007 | Steel | |
| 2007/0118973 A1 | 5/2007 | Lambertz | |
| 2007/0253962 A1 | 11/2007 | Hirsch et al. | |
| 2007/0256215 A1* | 11/2007 | Lambertz | 2/239 |
| 2008/0295216 A1 | 12/2008 | Nordstrom et al. | |
| 2009/0005717 A1* | 1/2009 | Brzank | 602/65 |
| 2009/0106879 A1* | 4/2009 | Post | 2/240 |
| 2009/0300823 A1* | 12/2009 | Connaghan et al. | 2/241 |
| 2010/0050322 A1* | 3/2010 | Zagula | 2/239 |
| 2011/0000006 A1 | 1/2011 | Fehring | |
| 2011/0082403 A1* | 4/2011 | Hill | 602/28 |

* cited by examiner

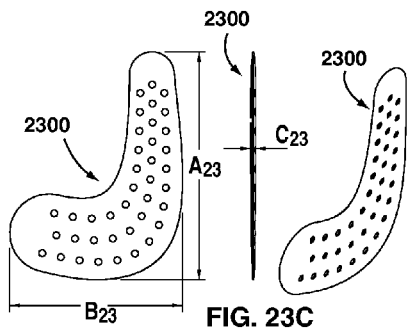
| Stabilizer Pad - Ski/Hockey | | | | | | | | | |
|---|---|---|---|---|---|---|---|---|---|
| | 2mm L | 2mm M | 2mm S | 4mm L | 4mm M | 4mm S | 6mm L | 6mm M | 6mm S |
| $A_{23}$ | 108.16 | 99.51 | 90.86 | 108.16 | 99.51 | 90.86 | 108.16 | 99.51 | 90.86 |
| $B_{23}$ | 81.98 | 75.42 | 68.87 | 81.99 | 75.43 | 68.87 | 81.98 | 75.42 | 68.87 |
| $C_{23}$ | 2.49 | 2.49 | 2.49 | 4.24 | 4.23 | 4.23 | 6.44 | 6.44 | 6.44 |
FIG. 23A
FIG. 23B
FIG. 23C
FIG. 23D
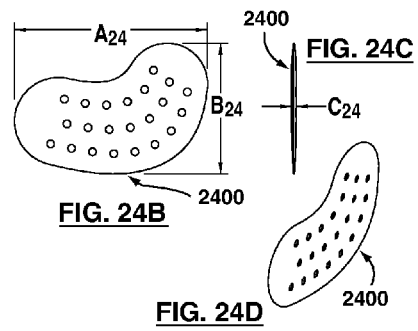
| Stabilizer Pad - Running | | | | | | | | | |
|---|---|---|---|---|---|---|---|---|---|
| | 2mm L | 2mm M | 2mm S | 4mm L | 4mm M | 4mm S | 6mm L | 6mm M | 6mm S |
| $A_{24}$ | 81.4 | 74.97 | 68.45 | 81.49 | 74.97 | 68.45 | 81.49 | 74.97 | 68.45 |
| $B_{24}$ | 55.21 | 50.79 | 46.38 | 55.21 | 50.79 | 46.38 | 55.21 | 50.79 | 46.38 |
| $C_{24}$ | 2.11 | 2.13 | 2.11 | 4.14 | 4.14 | 4.16 | 6.24 | 6.24 | 6.23 |
FIG. 24A
FIG. 24B
FIG. 24C
FIG. 24D

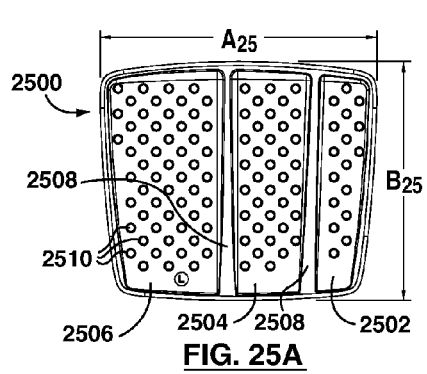
FIG. 25A
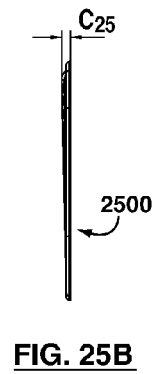
FIG. 25B
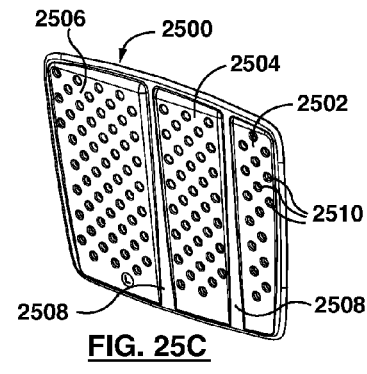
FIG. 25C
| Boot Bang Protector Pad - Left | | | | | | | | | |
|---|---|---|---|---|---|---|---|---|---|
| | 4mm L | 4mm M | 4mm S | 6mm L | 6mm M | 6mm S | 8mm L | 8mm M | 8mm S |
| $A_{25}$ | 123.46 | 113.58 | 103.7 | 123.4 | 113.58 | 103.62 | 123.62 | 113.73 | 103.84 |
| $B_{25}$ | 106.7 | 98.16 | 89.63 | 106.81 | 98.27 | 89.72 | 106.89 | 98.34 | 89.79 |
| $C_{25}$ | 3.96 | 3.96 | 3.96 | 5.94 | 5.94 | 5.94 | 7.88 | 7.88 | 7.88 |
FIG. 25D

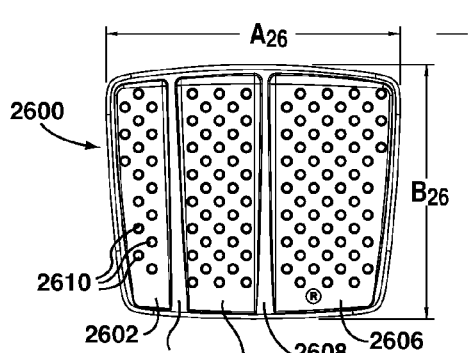
FIG. 26A
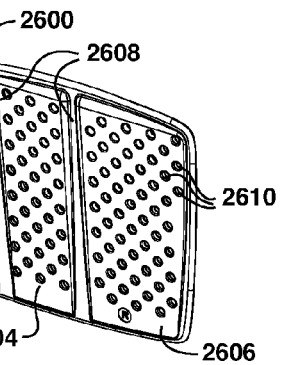
FIG. 26B
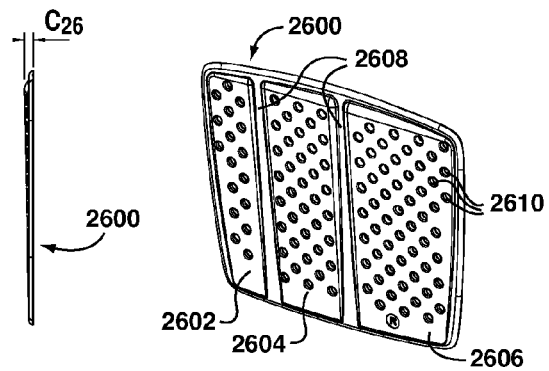
FIG. 26C
2612 →
| Boot Bang Protector Pad - Right | | | | | | | | | |
|---|---|---|---|---|---|---|---|---|---|
| | 4mm L | 4mm M | 4mm S | 6mm L | 6mm M | 6mm S | 8mm L | 8mm M | 8mm S |
| $A_{26}$ | 123.46 | 113.58 | 103.66 | 123.46 | 113.58 | 103.66 | 123.56 | 113.66 | 103.75 |
| $B_{26}$ | 106.82 | 98.27 | 89.72 | 106.73 | 98.19 | 89.65 | 106.83 | 98.29 | 89.74 |
| $C_{26}$ | 3.96 | 3.96 | 3.96 | 5.94 | 5.94 | 5.94 | 7.87 | 7.87 | 7.87 |
FIG. 26D

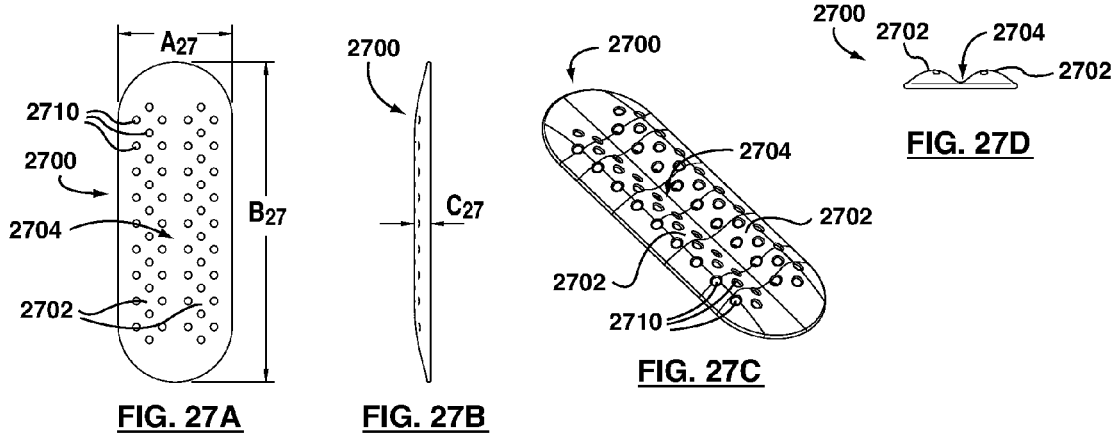

2812

| Running Socks - Lateral Side |||||||||||
|---|---|---|---|---|---|---|---|---|---|---|
| Left / Right Lateral Side | $A_{28}$ | $B_{28}$ | $C_{28}$ | $D_{28}$ | $E_{28}$ | $F_{28}$ | $G_{28}$ | $H_{28}$ | $I_{28}$ | $J_{28}$ | $K_{28}$ |
| SIZE (M) flattened after forming | 11.5 | 19.5 | 9.2 | 8 | 4.5 | 7.5 | 14 | 1 | 2.6 | 1.8 | 2.5 |
| SIZE (L) flattened after forming | 13.5 | 22.5 | 9.6 | 8 | 4.5 | 8 | 16 | 2.3 | 3.3 | 2 | 4 |
| SIZE (XL) flattened after forming | 13.5 | 24 | 10 | 8 | 4.5 | 7.7 | 17.7 | 3.3 | 2.7 | 1.8 | 5.6 |

| Running Socks - Medial Side |||||||||||
|---|---|---|---|---|---|---|---|---|---|---|
| Left / Right Medial Side | $A_{28}$ | $B_{28}$ | $C_{28}$ | $D_{28}$ | $E_{28}$ | $F_{28}$ | $G_{28}$ | $H_{28}$ | $I_{28}$ | $J_{28}$ | $K_{28}$ |
| SIZE (M) flattened after forming | 11.5 | 19.5 | 9.2 | 8 | 4.5 | 7.5 | 15 | 0.6 | 3 | 1.6 | 2.3 |
| SIZE (L) flattened after forming | 13.5 | 22.5 | 9.6 | 8 | 4.5 | 8 | 16.8 | 2.8 | 2.7 | 1 | 4 |
| SIZE (XL) flattened after forming | 13.5 | 24 | 10 | 8 | 4.5 | 7.7 | 17.5 | 2.5 | 3 | 2.6 | 5.4 |

| Hockey Socks - Lateral Side | | | | | | | | | | | | | | |
|---|---|---|---|---|---|---|---|---|---|---|---|---|---|---|
| Left / Right Lateral Side | $A_{30}$ | $B_{30}$ | $C_{30}$ | $D_{30}$ | $E_{30}$ | $F_{30}$ | $G_{30}$ | $H_{30}$ | $I_{30}$ | $J_{30}$ | $K_{30}$ | $L_{30}$ | $M_{30}$ | $N_{30}$ |
| SIZE (M) flattened after forming | 35 | 19.5 | 9 | 8.5 | 4.5 | 8 | 15.5 | 17.5 | 4 | 2.8 | 24.2 | 20.2 | 8 | 12 |
| SIZE (L) flattened after forming | 36.5 | 20 | 9.5 | 7.5 | 4.7 | 7 | 15 | 22.5 | 3.5 | 2 | 29.5 | 23 | 6.5 | 12.5 |
| SIZE (XL) flattened after forming | 41 | 22 | 9.5 | 8.5 | 4.5 | 8 | 17.5 | 25.5 | 2 | 1.5 | 22 | 24 | 8 | 14.5 |

| Hockey Socks - Medial Side | | | | | | | | | | | | | | |
|---|---|---|---|---|---|---|---|---|---|---|---|---|---|---|
| Left / Right Medial Side | $A_{30}$ | $B_{30}$ | $C_{30}$ | $D_{30}$ | $E_{30}$ | $F_{30}$ | $G_{30}$ | $H_{30}$ | $I_{30}$ | $J_{30}$ | $K_{30}$ | $L_{30}$ | $M_{30}$ | $N_{30}$ |
| SIZE (M) flattened after forming | 35 | 19.5 | 9 | 8.5 | 4.5 | 8 | 16.5 | 17 | 3.5 | 3 | 24 | 20.2 | 7 | 12 |
| SIZE (L) flattened after forming | 36.5 | 20 | 9.5 | 7.5 | 4.7 | 7 | 16 | 19.2 | 3.5 | 2.3 | 26.5 | 23 | 8 | 12.5 |
| SIZE (XL) flattened after forming | 41 | 22 | 9.5 | 8.5 | 4.5 | 8 | 16.5 | 25 | 3.7 | 3.5 | 21 | 24 | 6.3 | 14.5 |

| Ski Socks - Lateral Side | | | | | | | | | | | | | | |
|---|---|---|---|---|---|---|---|---|---|---|---|---|---|---|
| Left / Right Lateral Side | $A_{29}$ | $B_{29}$ | $C_{29}$ | $D_{29}$ | $E_{29}$ | $F_{29}$ | $G_{29}$ | $H_{29}$ | $I_{29}$ | $J_{29}$ | $K_{29}$ | $L_{29}$ | $M_{29}$ | $N_{29}$ |
| SIZE (M) flattened after forming | 35 | 19.5 | 9 | 8.5 | 4.5 | 8 | 15.15 | 17.5 | 4 | 2.8 | 24.2 | 6.3 | 14.2 | 26 |
| SIZE (L) flattened after forming | 36.5 | 20 | 9.5 | 7.5 | 4.7 | 7 | 15 | 22.5 | 3.5 | 2 | 29.5 | 7.2 | 5.2 | 27 |
| SIZE (XL) flattened after forming | 41 | 22 | 9.5 | 8.5 | 4.5 | 8 | 17.5 | 25.5 | 2 | 1.5 | 22 | 7.8 | 5.9 | 32.5 |

| Ski Socks - Medial Side | | | | | | | | | | | | | | |
|---|---|---|---|---|---|---|---|---|---|---|---|---|---|---|
| Left / Right Medial Side | $A_{29}$ | $B_{29}$ | $C_{29}$ | $D_{29}$ | $E_{29}$ | $F_{29}$ | $G_{29}$ | $H_{29}$ | $I_{29}$ | $J_{29}$ | $K_{29}$ | $L_{29}$ | $M_{29}$ | $N_{29}$ |
| SIZE (M) flattened after forming | 35 | 19.5 | 9 | 8.5 | 4.5 | 8 | 16.5 | 17 | 3.5 | 3 | 24 | 6.3 | 14 | 26 |
| SIZE (L) flattened after forming | 36.5 | 20 | 9.5 | 7.5 | 4.7 | 7 | 16 | 19.2 | 3.5 | 2.3 | 26.5 | 7.2 | 3 | 27 |
| SIZE (XL) flattened after forming | 41 | 22 | 9.5 | 8.5 | 4.5 | 8 | 16.5 | 25 | 3.7 | 3.5 | 21 | 7.8 | 3.9 | 32.5 |

| Running Socks - Stabilizer Pocket | | | | | | |
|---|---|---|---|---|---|---|
| | $A_{31}$ | $B_{31}$ | $C_{31}$ | $D_{31}$ | $E_{31}$ | $F_{31}$ |
| SIZE (M) | 74.97 | 50.8 | 2.22 | 2.26 | 4.00 | 26.00 |
| SIZE (L/XL) | 81.49 | 57.4 | 2.90 | 2.80 | 4.50 | 26.00 |

| Ski/Hockey Socks - Stabilizer Pocket | | | | | | |
|---|---|---|---|---|---|---|
| | $A_{32}$ | $B_{32}$ | $C_{32}$ | $D_{32}$ | $E_{32}$ | $F_{32}$ |
| SIZE (M) | 75.43 | 99.51 | 2.45 | 26.00 | 4.00 | 2.43 |
| SIZE (L/XL) | 85.73 | 108.16 | 2.25 | 26.00 | 4.50 | 2.53 |

| Ski Socks - Boot Bang Pocket | | | | | | | | |
|---|---|---|---|---|---|---|---|---|
| | $A_{33}$ | $B_{33}$ | $C_{33}$ | $D_{33}$ | $E_{33}$ | $F_{33}$ | $G_{33}$ | $H_{33}$ |
| SIZE (M) | 113.66 | 98.29 | 16.3 | 22.9 | 16.3 | 22.9 | 55.0 | 6.0 |
| SIZE (L/XL) | 123.6 | 106.88 | 20.9 | 28.2 | 20.9 | 28.2 | 55.0 | 6.0 |

| Hockey Socks - Lace Bite Pad Pocket | | | | | |
|---|---|---|---|---|---|
| | $A_{35}$ | $B_{35}$ | $C_{35}$ | $D_{35}$ | $E_{35}$ |
| SIZE (M) | 42.00 | 117.60 | 4.00 | 30.00 | 2.00 |
| SIZE (L/XL) | 49.5 | 136.00 | 5.00 | 34.00 | 3.00 |

# FOOT STABILIZER SOCKS AND STABILIZER PADS THEREFOR

CROSS-REFERENCE TO RELATED APPLICATION

This application claims priority to U.S. Provisional Application No. 61/264,621 filed Nov. 25, 2009, the teachings of which are hereby incorporated by reference in their entirety.

FIELD OF INVENTION

The present invention relates to stabilization of a human foot within a piece of footwear, and more particularly to socks and stabilizer pads for such stabilization.

BACKGROUND OF THE INVENTION

The foot is the foundation on which the human body interacts with, and distributes, forces from the ground. It is a complex system made up of twenty-six bones, thirty-three joints and hundreds of muscles, tendons and ligaments. To function properly, all of these complex systems must work together, and a malfunction in any part of the foot may also manifest itself in other locations in the body.

Structurally, the foot has three main parts: the rearfoot, the midfoot and the forefoot. With reference now to FIGS. 1 to 4, an exemplary skeletal foot is shown generally at 10, and comprises rearfoot 12, midfoot 14, and forefoot 16. The skeletal structure of the rearfoot 12 comprises two bones, namely the talus 18 and the calcaneous 20, as well as three joints. These three joints are the talocrural joint 22, between the upper portion of the talus 18 and the lower tibia 24, the subtalar joint 26, between the lower portion of the talus 18 and the upper portion of the calcaneous 20, and the midtarsal joint, which, although conventionally referred to as a single joint, comprises the medial joints 28A between the talus 18 and the navicular bone 32, and the lateral joint 28B between the calcaneous 20 and the navicular bone 32. The midfoot 14 comprises five bones, namely the navicular bone 32, the cuboid bone 34 and three cuneiform bones 36, and forms the arch 38 of the foot 10. The forefoot 16 comprises nineteen bones, namely five metatarsal bones 40 and fourteen phalange bones 42. The fibular malleolus (also referred to as the lateral malleolus because of its position on the lateral side of the foot), which is a protrusion at the lower end of the fibula, is indicated with the reference numeral 46. Similarly, the tibial malleolus (also referred to as the medial malleolus because of its position on the medial side of the foot) is a protrusion at the lower end of the tibia and is indicated with the reference numeral 48.

The movements of the foot 10 relative to the ankle are primarily controlled by way of the rearfoot 10. The primary movements of the talocrural joint 22 are plantar flexion (downward movement of the foot 10) and dorsiflexion (upward movement of the foot 10). These movements take place in the sagittal plane and are important for the movement of the foot and ankle. The movements supported by the subtalar joint 26 are complex; the primary movements enabled by the subtalar joint 26 are inversion (turning the bottom or sole of the foot 10 inward) and eversion (turning the bottom or sole of the foot outward). The subtalar joint 26 creates movements in all three cardinal planes and functions like a mitred hinge. with simultaneous motion in all three cardinal planes. As the subtalar joint 26 moves into eversion, the tibia 24 rotates.

These four movements, plantar flexion, dorsiflexion, inversion and eversion, along with adduction (twisting the foot 10 inward) and abduction (twisting the foot 10 outward) are involved with two main movements during the gait cycle (i.e. walking or running), namely pronation and supination. Pronation is the combination of dorsiflexion, abduction and eversion. Supination is the combination of plantar flexion, adduction and inversion. Supination and pronation are commonly used to define foot alignment under a weight bearing ("closed-chain") condition. These motions are important to proper movement of the foot 10 throughout the entire gait cycle.

The gait cycle can be divided into three main components. The first is heel strike, which is the period of time in which the calcaneous 20 (the heel) strikes the ground (or other surface) and the rest of the foot 10, i.e. the midfoot 14 and forefoot 16, moves toward the ground. The second stage is midstance, which is the point at which the bottom of the entire foot 10, that is, rearfoot 12, midfoot 14 and forefoot 16, is on the ground. The third stage is toe-off, which is the point at which the foot 10 is preparing to leave the ground, and only the bottom of the forefoot 16 remains in contact with the ground.

During heel strike the foot 10 is in a supinated position, which allows the twenty-six bones to be "locked" so that the foot 10 will have a stable base of support as the calcaneous 20 hits the ground. As the gait cycle progresses to midstance, the foot 10 transitions from the "locked", supinated position to an "unlocked" pronated position, to allow the foot 10 to accommodate uneven surfaces. As the foot 10 transitions to toe-off, the foot 10 returns to the supinated position to give the foot 10 a stable base of support to push off the ground. Throughout the gait cycle, the foot 10 is in constant motion allowing for both stability and flexibility.

The subtalar joint 26 (see FIG. 1) plays an important role in the foot 10, both statically and dynamically, because of its central role in pronation and supination, and also because it can convert foot rotation into leg rotation and leg rotation into foot rotation. The subtalar joint 26 therefore has a direct role not only in the function of the foot 10, but also the knees, the hips and the pelvis, and an indirect role in respect of areas above the pelvis including the lower back.

SUMMARY OF THE INVENTION

In one aspect, the present invention is directed to a sock. The sock has a foot section having a shape corresponding to a human foot and comprising a rearfoot portion corresponding to human calcaneous and talus bones and to tibial and fibular malleoli, a forefoot portion corresponding to human metatarsal and phalanx bones, and a midfoot portion between the rearfoot portion and the forefoot portion and corresponding to human cuboid, navicular and cuneiform bones. The sock has a medial stabilizer region on a medial side of the sock corresponding to a medial side of the foot and a lateral stabilizer region on a lateral side of the sock corresponding to a lateral side of the foot. In one embodiment, the medial stabilizer region and the lateral stabilizer region are separate and distinct from one another. The medial stabilizer region covers a forward medial region of the rearfoot portion and a rearward medial region of the midfoot portion, and the lateral stabilizer region covers a forward lateral region of the rearfoot portion.

In one embodiment, the medial stabilizer region extends from a position on the rearfoot portion corresponding to a position on the foot posterior to the tibial malleolus and anterior to the Achilles tendon, across a part of the rearfoot portion corresponding to the lower medial part of the talus and the upper medial part of the calcaneous, to terminate at a position on the midfoot portion corresponding to the navicular bone, and the lateral stabilizer region extends from a position on the rearfoot portion corresponding to a position on the foot posterior to the fibular malleolus and anterior to the Achilles tendon, across a lower part of the rearfoot portion corresponding to a lower lateral part of the talus and the upper lateral part of the calcaneous. The medial stabilizer region preferably includes a medial malleolal concavity at its upper edge to accommodate the tibial malleolus, and the lateral stabilizer region preferably includes a lateral malleolal concavity at its upper edge to accommodate the fibular malleolus.

In one embodiment, the lateral stabilizer region extends to and terminates at a position on the rearfoot portion corresponding to a position on the foot posterior and proximal to the cuboid bone.

In one embodiment, the sock includes a leg section corresponding at least to the lower portions of the human tibia and fibula bones. In such an embodiment, the lateral stabilizer region may extend from a position corresponding to a lateral position posterior to the fibular malleolus, anterior to the Achilles tendon, along an area of the leg section corresponding to a lower posterior part of the fibula, and the medial stabilizer region may extend from a position corresponding to a medial position posterior to the tibial malleolus, anterior to the Achilles tendon, along an area of the leg section corresponding to a lower posterior part of the tibia.

Each of the medial stabilizer region and the lateral stabilizer region may consist of a pocket for receiving, respectively, a medial stabilizer pad and a lateral stabilizer pad, or may consist of a region over which is secured a textile selected from a group consisting of hook-surfaced textile and loop-surfaced textile. A medial stabilizer pad corresponding in size and shape to the medial stabilizer region may be secured to the sock at the medial stabilizer region and a lateral stabilizer pad corresponding in size and shape to the lateral stabilizer region may be secured to the sock at the lateral stabilizer region. The medial stabilizer region and the lateral stabilizer region may also comprise portions of the sock having material that is substantially thickened, relative to surrounding material, to form protrusions that define the medial stabilizer region and lateral stabilizer region.

In another aspect, the present invention is directed to a stabilizer pad for a human foot that includes a rearfoot comprising calcaneous and talus bones and tibial and fibular malleoli and a midfoot comprising human cuboid, navicular and cuneiform bones. The stabilizer pad is shaped to, when positioned adjacent the medial part of the foot consisting of the forward medial region of the rearfoot and the rearward medial region of the midfoot, extend from a position on the foot posterior to the tibial malleolus and anterior to the Achilles tendon, across the lower medial part of the talus and the upper medial part of the calcaneous to terminate at the navicular bone. A malleolal concavity may be defined in the upper edge of the stabilizer pad to accommodate the tibial malleolus. The stabilizer pad may be formed from a material comprising silicone, or from foam, or may comprise a gel-filled enclosure.

In a further aspect, the present invention is directed to a stabilizer pad for a human foot that includes a rearfoot comprising calcaneous and talus bones and tibial and fibular malleoli and a midfoot comprising human cuboid, navicular and cuneiform bones. The stabilizer pad is shaped to, when positioned adjacent the forward lateral region of the rearfoot, extend from a position on the foot posterior to the fibular malleolus and anterior to the Achilles tendon, across a lower lateral part of the talus and an upper lateral part of the calcaneous. A malleolal concavity may be defined in the upper edge of the stabilizer pad to accommodate the fibular malleolus. The stabilizer pad may be formed from a material comprising silicone, or from foam, or may comprise a gel-filled enclosure.

In a still further aspect, the present invention is directed to a kit for assembling a stabilizer sock. The kit comprises at least one sock as described above, and a plurality of stabilizer pads of various thicknesses. Each stabilizer pad has a perimeter shape matching a perimeter shape of at least one of the medial stabilizer region and the lateral stabilizer region and is securable at the corresponding at least one of the medial stabilizer region and the lateral stabilizer region. The kit may further comprise instructions for selecting stabilizer pads and securing the selected stabilizer pads at the medial stabilizer region and the lateral stabilizer region.

In yet a further aspect, the present invention is directed to a foot-supporting sock system. The foot-supporting sock system comprises a sock and two opposed reniform pads disposed on opposite sides of the sock. In one embodiment, the sock has a closed toe end and an open foot insertion end, and each reniform pad has a first end pointing generally toward the closed toe end of the sock and a second end pointing generally toward the open foot insertion end of the sock. The foot-supporting sock system may further comprise a set of pockets affixed to the sock, with each of the pockets enclosing a corresponding one of the pads. In a particular embodiment, each of the pockets includes an opening at a portion of the pocket opposite a surface of the sock to which the pocket is affixed, with each opening permitting removal of the respective enclosed pad.

In still yet a further aspect, the present invention is directed to a foot-supporting sock system comprising a sock and two opposed reniform pockets disposed on opposite sides of the sock. In one embodiment, the sock has a closed toe end and an open foot insertion end, and each reniform pocket has a first end pointing generally toward the closed toe end of the sock and a second end pointing generally toward the open foot insertion end of the sock. The foot-supporting sock system may further comprise a set of reniform pads each of which is enclosed in a corresponding one of the pockets. In a particular embodiment, each of the pockets includes an opening at a portion of the pocket opposite a surface of the sock to which the pocket is affixed, with each opening permitting removal of the respective enclosed pad.

BRIEF DESCRIPTION OF THE DRAWINGS

These and other features of the invention will become more apparent from the following description in which reference is made to the appended drawings wherein:

FIG. 23A is a table showing exemplary dimensions for a stabilizer pad for skiing and hockey socks according to an aspect of the present invention;

FIGS. 23B to 23D are top, side and perspective views of a stabilizer pad for ski and hockey socks according to an aspect of the present invention, corresponding to the dimensions shown in the table of FIG. 23A;

FIG. 24A is a table showing exemplary dimensions for a stabilizer pad for running socks according to an aspect of the present invention;

FIGS. 24B to 24D are top, side and perspective views of a stabilizer pad for running socks according to an aspect of the present invention, corresponding to the dimensions shown in the table of FIG. 24A;

FIGS. 25A to 25C are top, side and perspective views of a left side boot bang protector pad, according to an aspect of the present invention;

FIG. 25D shows a table containing exemplary dimensions for the boot bang protector pad of FIGS. 25A to 25C;

FIGS. 26A to 26C are top, side and perspective views of a right side boot bang protector pad, according to an aspect of the present invention;

FIG. 26D shows a table containing exemplary dimensions for the boot bang protector pad of FIGS. 26A to 26C;

FIGS. 27A to 25D are top, side, perspective and end views of a lace bite protector pad, according to an aspect of the present invention;

FIG. 27E shows a table containing exemplary dimensions for the lace bite protector pad of FIGS. 27A to 27D;

FIG. 28B shows two tables containing exemplary dimensions of the running sock of FIG. 28A;

FIG. 29B shows two tables containing exemplary dimensions of the hockey sock of FIG. 29A;

FIG. 30B shows two tables containing exemplary dimensions of the skiing sock of FIG. 30A;

DETAILED DESCRIPTION

As will be described in greater detail below, according to an aspect of the invention foot stabilizer socks may be provided with stabilizer pads that are carefully anatomically positioned to improve the interface between the user's foot and lower leg and a piece of outer footwear, such as a shoe, boot, skate, or the like.

Figure 1:
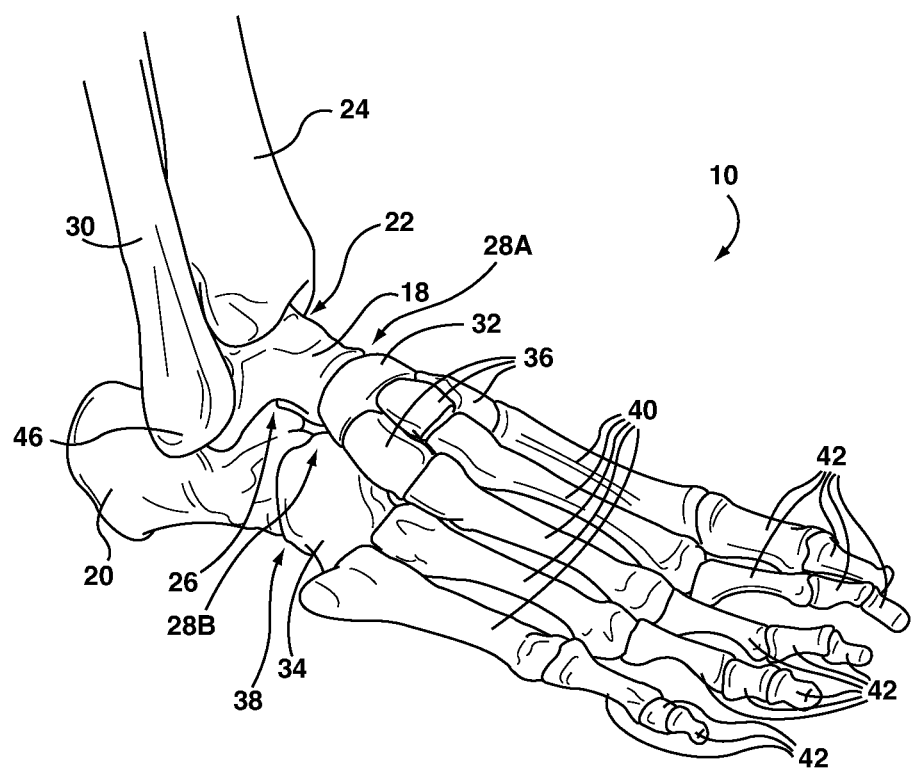
FIG. 1 is a perspective view of a skeletal human right foot from the lateral side thereof.
Figure 2:
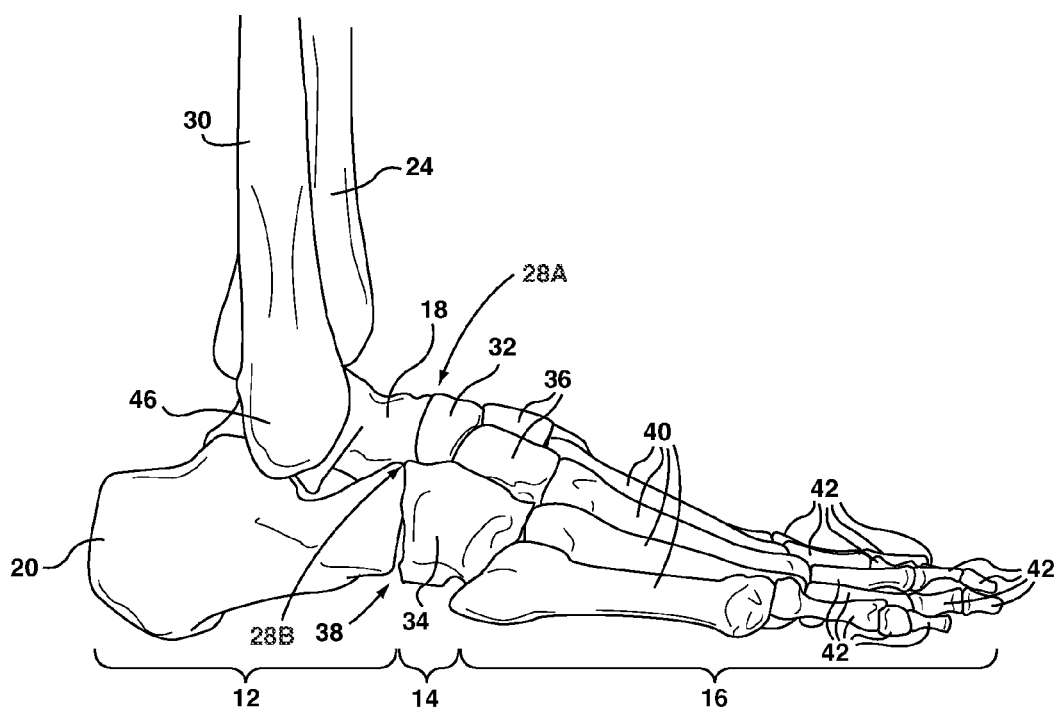
FIG. 2 is a lateral view of the human foot of FIG. 1.
Figure 3:
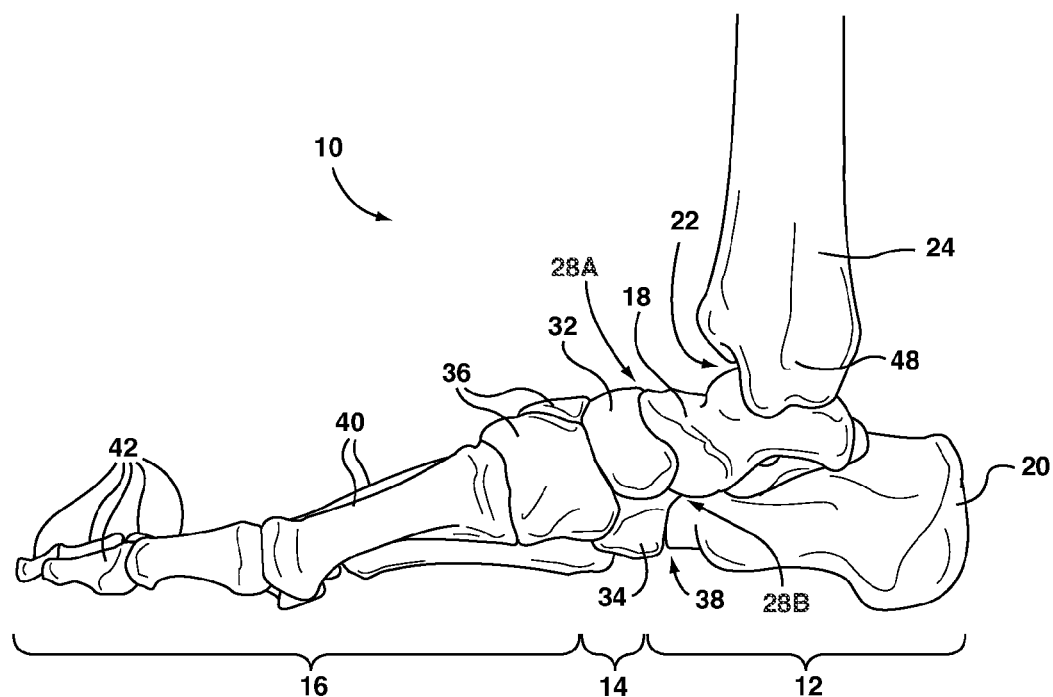
FIG. 3 is a medial view of the human foot of FIG. 1.
Figure 4:
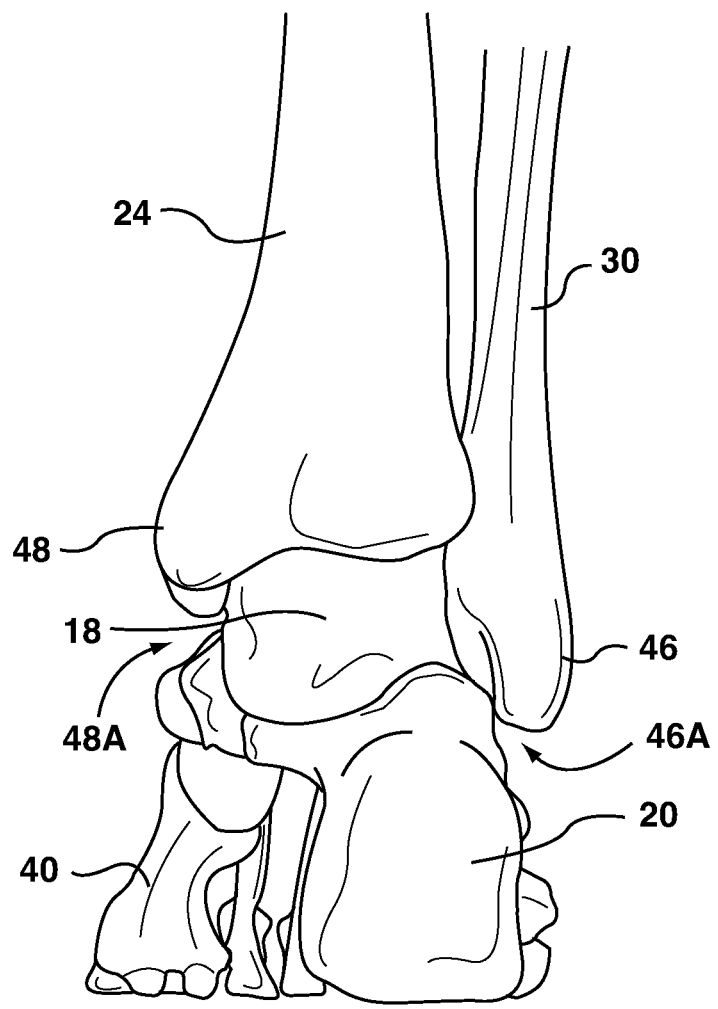
FIG. 4 is a rear view of the human foot of FIG. 1.
Figure 5:
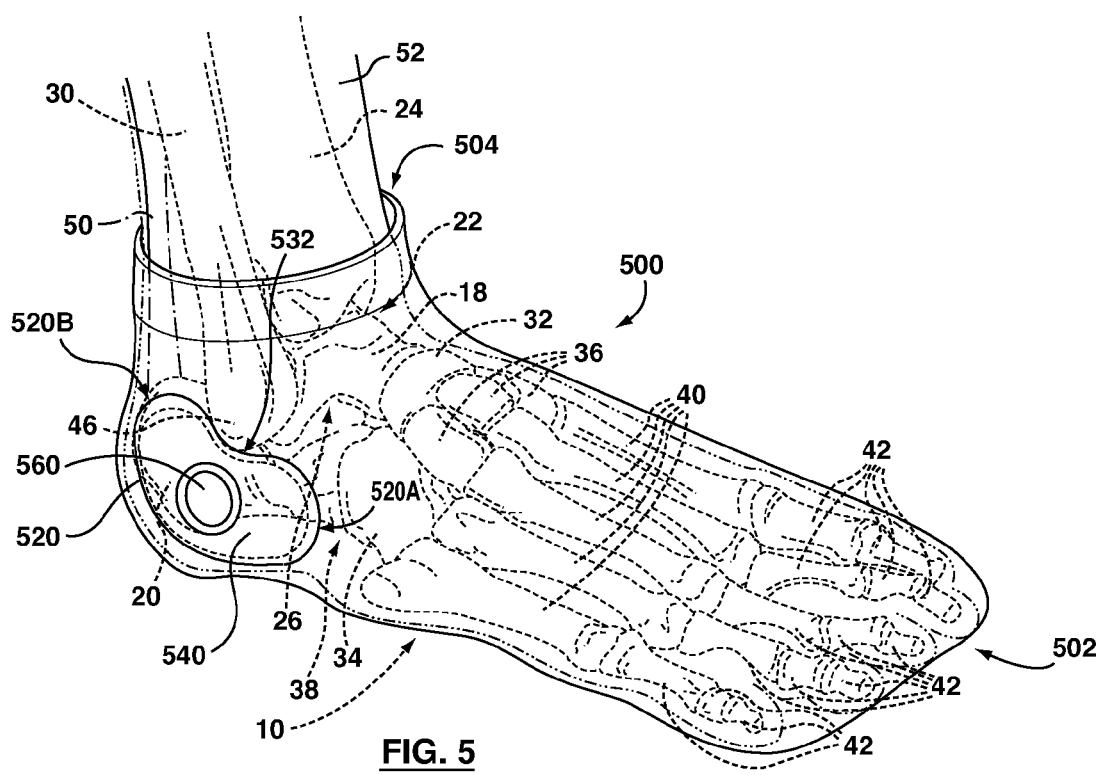
FIG. 5 is a is a perspective view of a first exemplary embodiment of a foot stabilizer sock, according to an aspect of the present invention, with a human right foot inside thereof.

As can be seen best by reference to FIG. 4, the skeletal structure of a human foot results in certain recessed portions of a the foot, such as the regions 46A, 48A immediately below the fibular malleolus 46 and the tibial malleolus 48, respectively. Because the shape of outer footwear is generally constrained by the outer boundaries of the foot 10, the recessed regions 46A, 48A may result in gaps between the foot and the outer footwear, where the foot is unsupported. This situation is undesirable, as it reduces the stability of the interface between the foot 10 and the outer footwear.

With reference now to FIGS. 5 to 8, a first exemplary foot stabilizer sock is shown generally at 500. The first foot stabilizer sock 500 includes a foot section denoted generally at 510 which has a shape corresponding to a human foot, and has a closed toe end 502 and an open foot insertion end 504. A human lower leg 52, including a human foot whose skeleton 10 is shown in dotted lines, is shown inside the sock 500, to show relative positioning of portions of the first foot stabilizer sock 500; it is understood that a human foot of course forms no part of the present invention.

Figure 6:
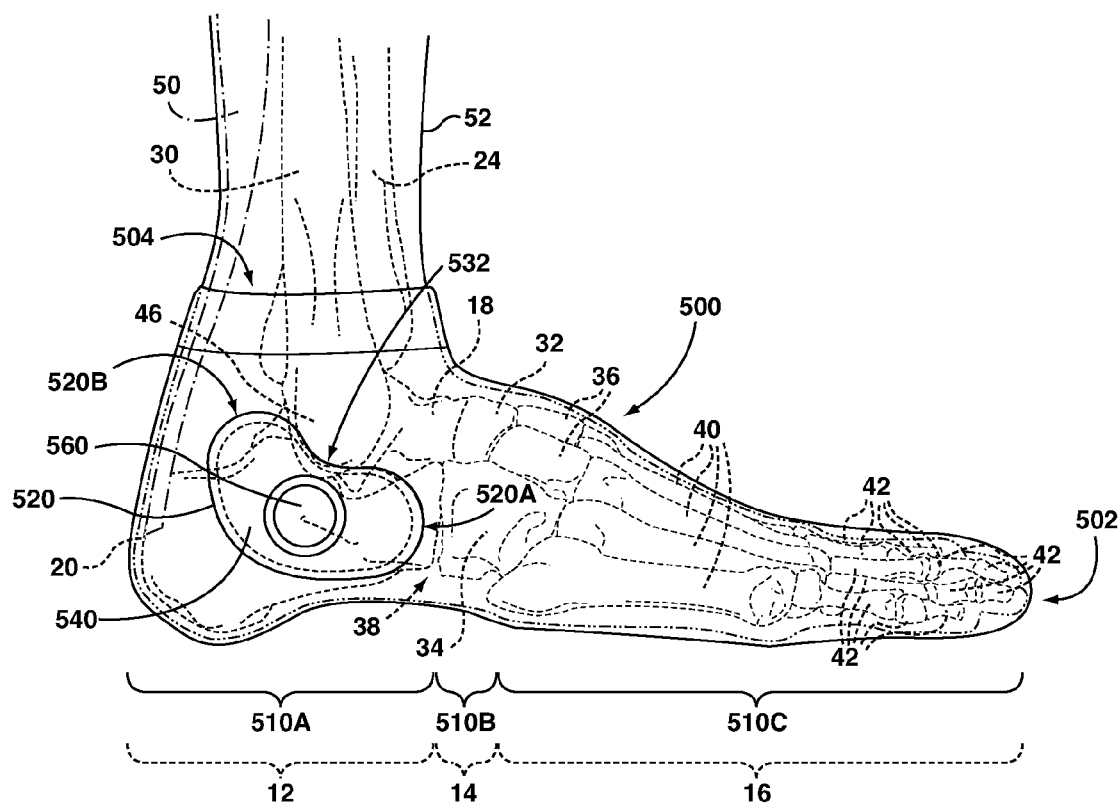
FIG. 6 is a lateral view of the foot stabilizer sock of FIG. 5.
Figure 7:
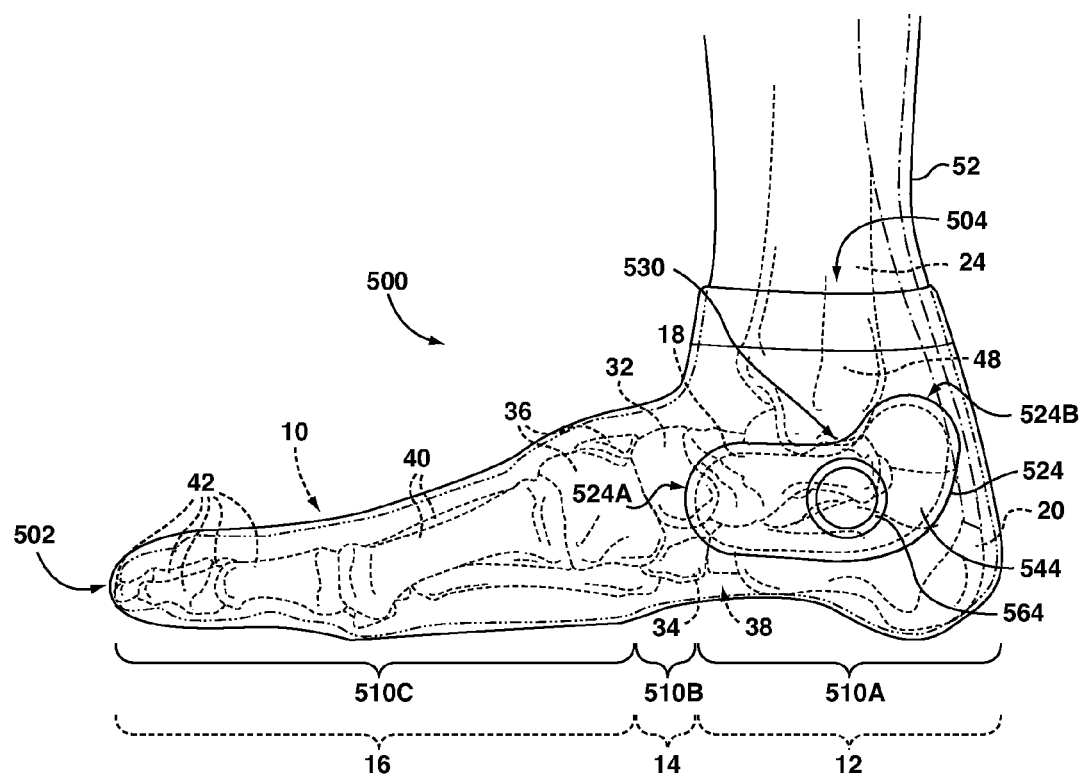
FIG. 7 is a medial view of the foot stabilizer sock of FIG. 5.
Figure 8:
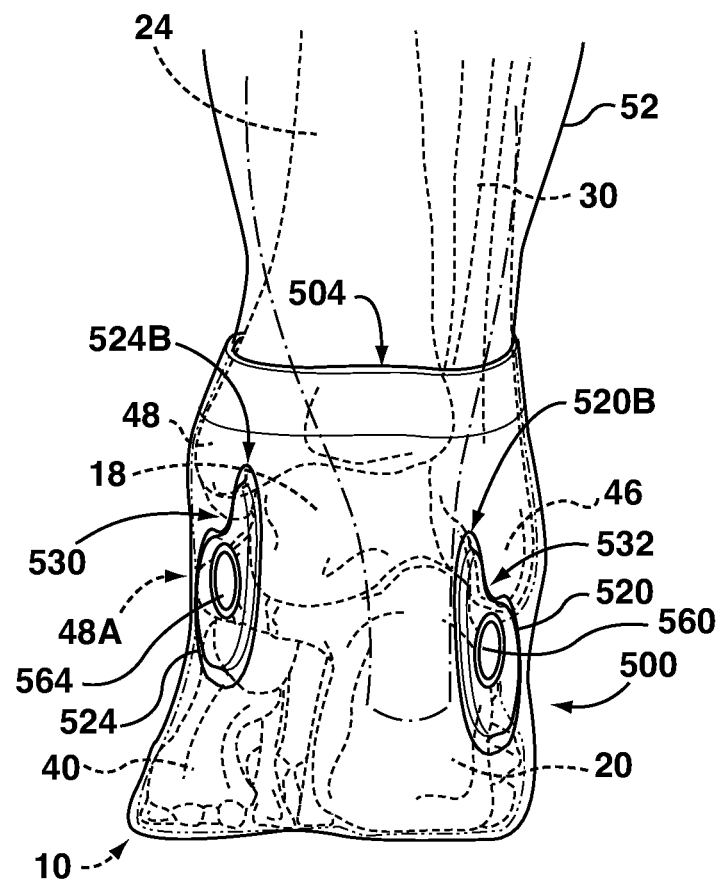
FIG. 8 is a rear view of the foot stabilizer sock of FIG. 5.

As shown in FIGS. 6 and 7, the foot section 510 comprises a rearfoot portion 510A, a midfoot portion 510B, and a forefoot portion 510C. The rearfoot portion 510A corresponds in position to the human calcaneous 20 and talus 18 and to the fibular and tibial malleoli 46, 48, respectively. The midfoot portion 510B corresponds in position to human navicular, cuboid and cuneiform bones 32, 34, 36, respectively, and the forefoot portion 510C corresponds to human metatarsal and phalanx bones 40, 42, respectively. The midfoot portion 510B is positioned between the rearfoot portion 510A and the forefoot portion 510C.

The first foot stabilizer sock 500 has a generally reniform lateral stabilizer region 520 on a lateral side of the foot stabilizer sock 500, corresponding to the lateral side of the foot 10, and a generally reniform medial stabilizer region 524 on a medial side of the foot stabilizer sock 500, corresponding to the medial side of the foot 10. In the illustrated embodiment, the lateral stabilizer region 520 and the medial stabilizer region 524 are separate and distinct from one another. The medial stabilizer region 524 has a first end 524A pointing generally towards the closed toe end 502 of the foot stabilizer sock 500, and a second end 524B pointing generally toward the open foot-insertion end of the foot stabilizer sock 500. Similarly, the lateral stabilizer region 520 has a first end 520A pointing generally towards the closed toe end 502 of the foot stabilizer sock 500, and a second end 520B pointing toward the open foot-insertion end 504 of the foot stabilizer sock 500.

As can best be seen in FIG. 6, the lateral stabilizer region 520 covers a forward lateral region of the rearfoot portion 510A, and as shown in FIG. 7, the medial stabilizer region 524 covers a forward medial region of the rearfoot portion 510A and a rearward media region of the midfoot portion 510B.

The lateral stabilizer region 520 extends from a position on the rearfoot portion 510A corresponding to a position on the human foot 10 that is posterior to the fibular malleolus 46 and anterior to the Achilles tendon 50, across a lower part of the rearfoot portion 510A corresponding to a lower lateral part of the talus 18 and an upper lateral part of the calcaneous 20. The medial stabilizer region 524 extends from a position on the rearfoot portion 510A corresponding to a position on the human foot 10 that is posterior to the tibial malleolus 48 and anterior to the Achilles tendon 50, across a part of the rearfoot portion 510A corresponding to a lower medial part of the talus 18 and an upper medial part of the calcaneous 20, to terminate at a position on the midfoot portion 510B corresponding to the navicular bone 32. In the illustrated embodiment, the medial stabilizer region 524 includes a medial malleolal concavity 530 at its upper edge to accommodate the tibial malleolus 48, and the lateral stabilizer region 520 includes a lateral malleolal concavity 532 at its upper edge to accommodate the fibular malleolus 46. The lateral stabilizer region 520 extends to and terminates at a position on the rearfoot portion 510A corresponding to a position on the human foot 10 that is posterior and proximal to the cuboid bone 34.

In the particular illustrated embodiment shown in FIGS. 5 to 8, the medial stabilizer region 524 and the lateral stabilizer region 520 each consist of a pocket 544, 540, respectively, secured to the sock 500 for receiving, respectively, a generally reniform medial stabilizer pad and a generally reniform lateral stabilizer pad so that each pad is enclosed in a corresponding one of the pockets. In the illustrated embodiment, the pads are inserted into, and can be removed from, the pockets 540, 544 by way of respective stretchable circular apertures 560, 564 located at a portion of the respective pocket 540, 544 opposite a surface of the sock 500 to which the pocket 540, 544 is affixed. Thus, there is provided a foot-supporting sock system comprising the foot stabilizer sock 500 and the two opposed reniform pockets 544, 540 disposed on opposite sides of the sock 500.

Figure 9A:
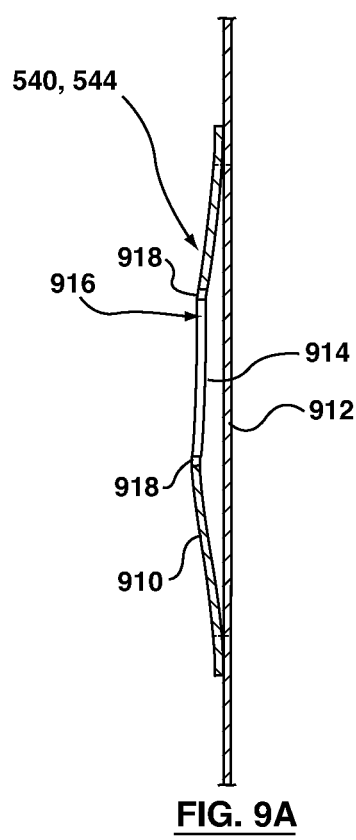
FIG. 9A is a cross-sectional view of an exemplary stabilizer region comprising a pocket, according to an aspect of the present invention.

As shown in FIG. 9A, the pockets 540, 544 are formed by securing an outer layer 910 made from stretchable material to the underlying material 912 of the sock 500, to define a cavity 914 for receiving a pad (not shown in FIG. 9A). The outer layer 910 can be secured to the underlying material 912 of the sock 500 by any suitable technique, including without limitation stitching, heat sealing, RF or infrared welding, and adhesive. The outer layer 910 includes an aperture 916 having a reinforced edge or edges 918, through which a pad (not shown in FIG. 9A) can be inserted into the cavity 914. Because the outer layer 910 is made from stretchable material, the aperture 916 can be stretched to permit insertion of the pad, after which the aperture 916 will return to its nominal size so that the pad will be retained in the cavity 914. Thus, a medial stabilizer pad 924 (see FIG. 9C), corresponding in size and shape to the medial stabilizer region, may be removably secured to the sock 500 at the medial stabilizer region 524, and a lateral stabilizer pad 920 (see FIG. 9B), corresponding in size and shape to the lateral stabilizer region 520, may be removably secured to the sock 500 at the lateral stabilizer region, in each case by insertion into the appropriate pocket.

Figure 9B:
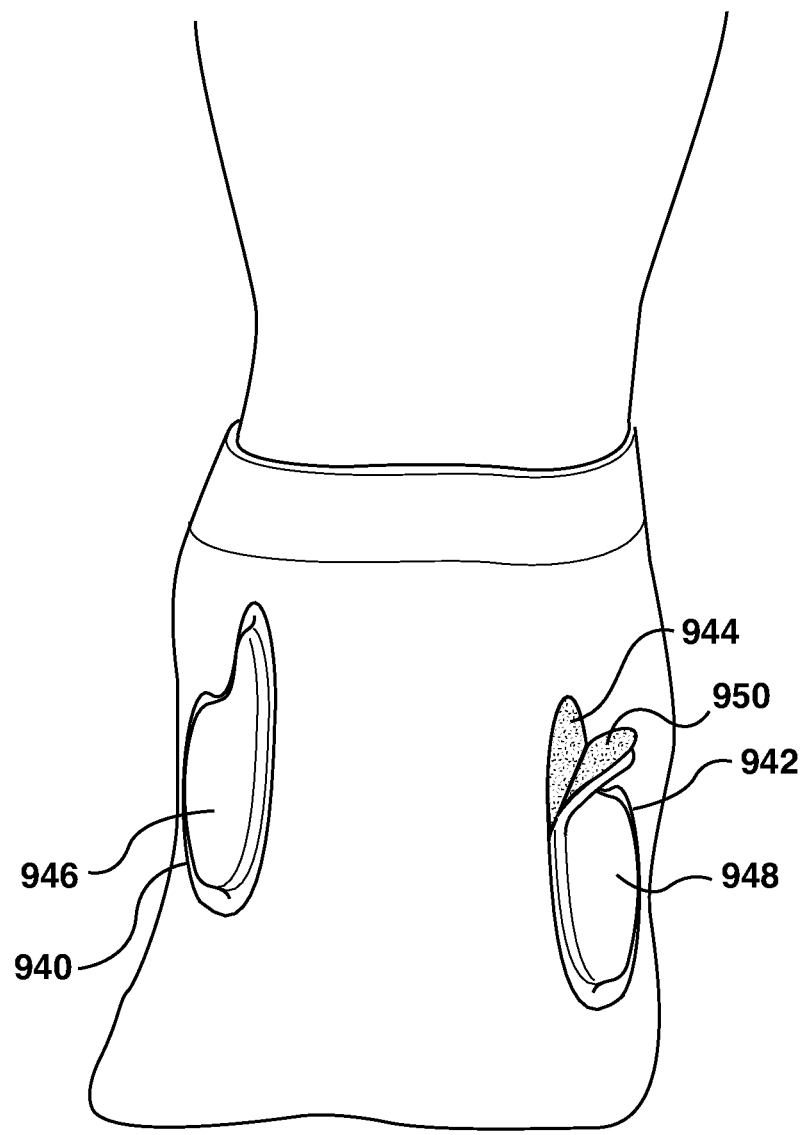
FIG. 9B is a rear view of a first modified embodiment of the foot stabilizer sock of FIG. 5, with a human right foot inside thereof.

Alternatively, as shown in FIG. 9B, the medial stabilizer region and the lateral stabilizer region may each consist of a region 940, 942, respectively, over which is secured a textile 944 selected from a group consisting of hook-surfaced textile and loop-surfaced textile. Correspondingly shaped medial and lateral stabilizer pads 946, 948, having complementary textile 950 (i.e. hook-surfaced if the textile 944 is loop-surfaced, and loop-surfaced if the textile 944 is hook surfaced) on one side thereof may be removably secured to the medial stabilizer region 940 and the lateral stabilizer region 942 by interaction between the hook surfaces and the loop surfaces.

Figure 9C:
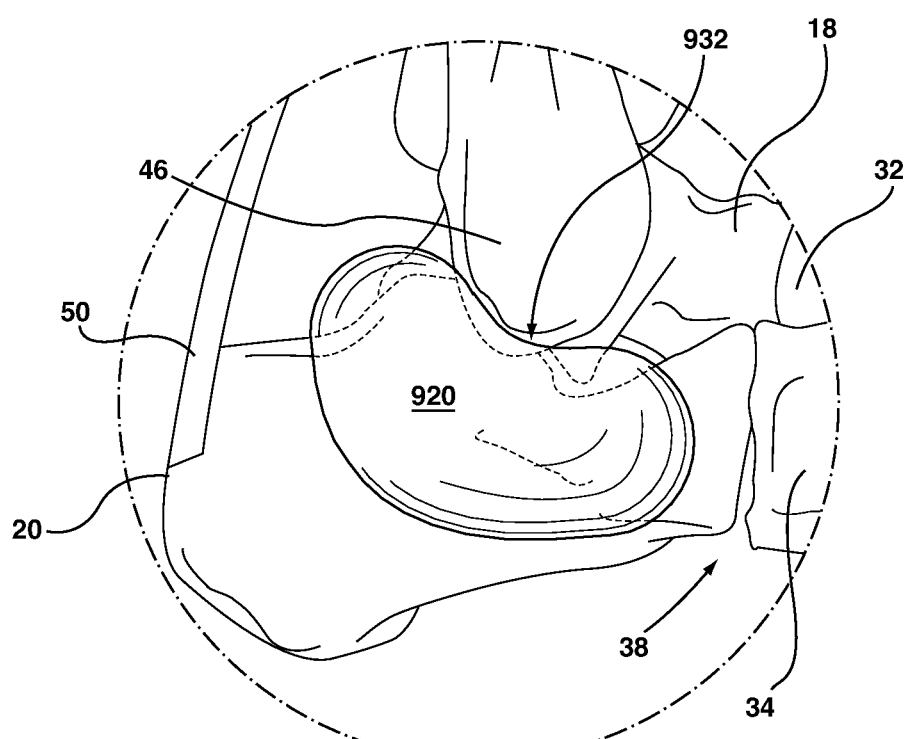
FIG. 9C shows a first exemplary lateral stabilizer pad, positioned relative to the lateral side of a skeletal human right foot.
Figure 9D:
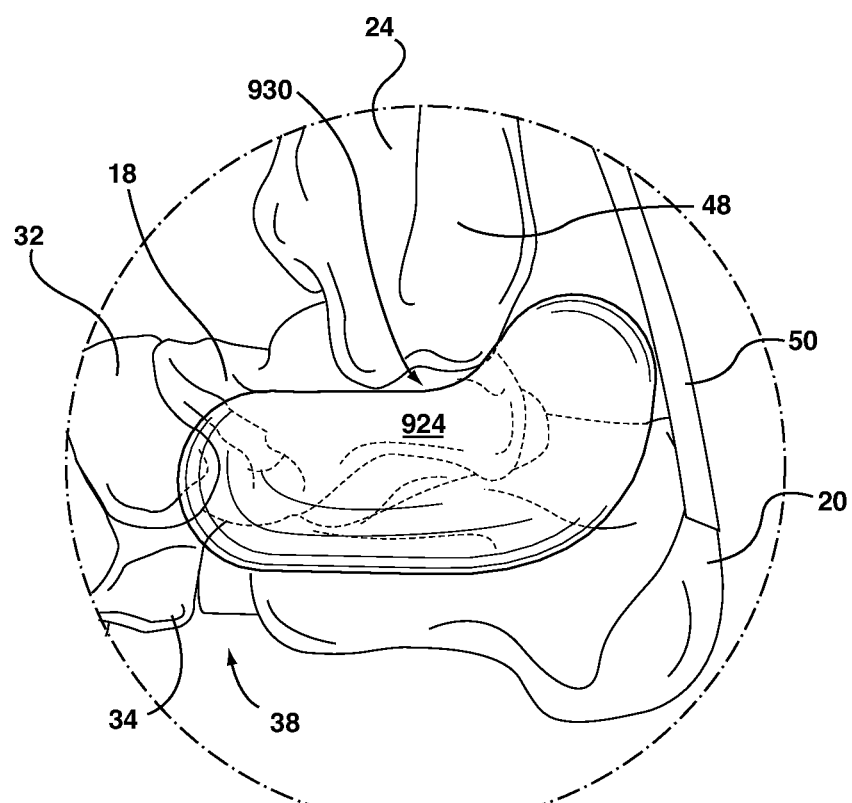
FIG. 9D shows a first exemplary medial stabilizer pad, positioned relative to the medial side of a skeletal human right foot.
Figure 9E:
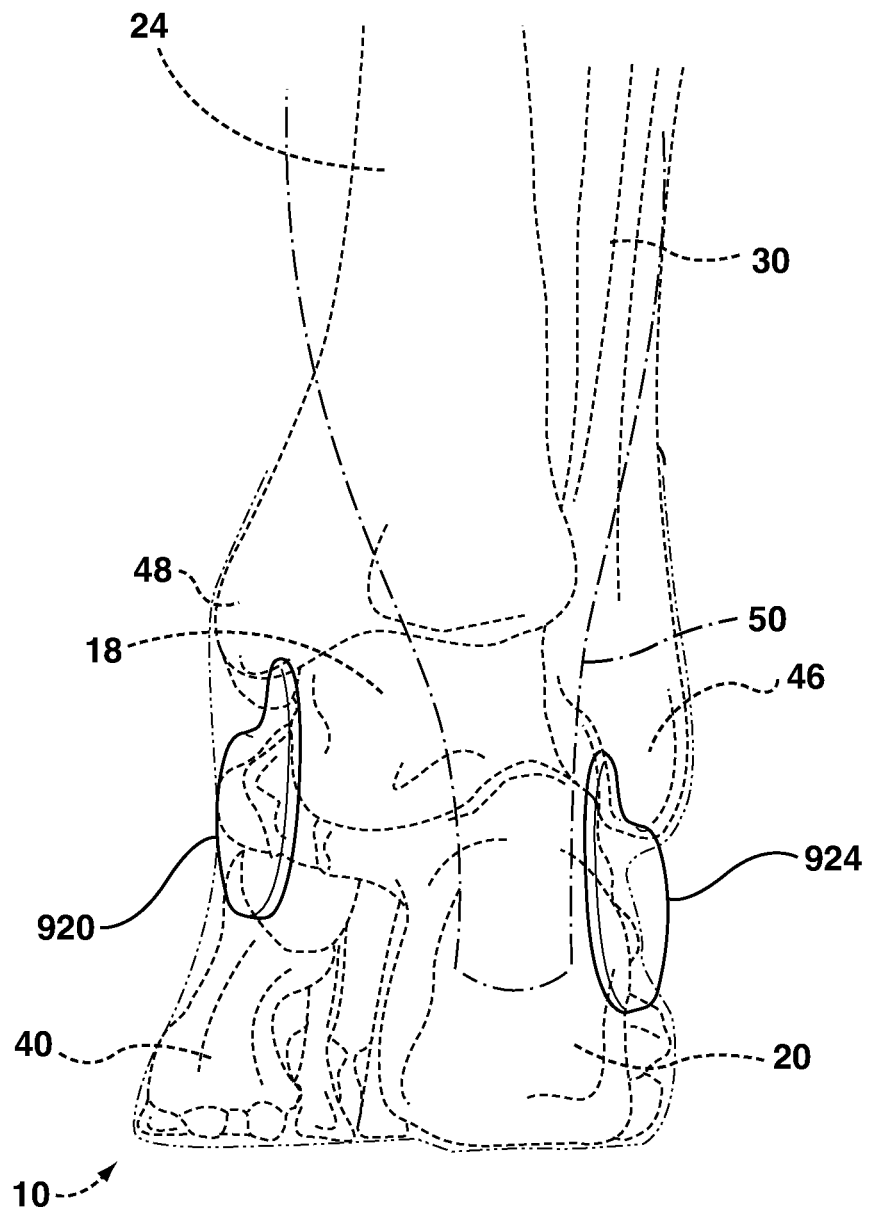
FIG. 9E shows the lateral stabilizer pad of FIG. 9C and the medial stabilizer pad of FIG. 9D, positioned relative to the rear of a skeletal human foot.

Exemplary stabilizer pads for use with a stabilizer sock according to an aspect of the present invention, such as the first stabilizer sock 500, are shown in FIGS. 9C, 9D and 9E. It will be understood that the stabilizer pads may come in different sizes, so that an appropriate size of pad may be selected for the size of the foot with which it is to be used. For example, there could be two different sizes of stabilizer pad (small and large), three sizes (small, medium and large), and so on, or a "one-size fits all" approach may be used. In addition, stabilizer pads may have sizes across multiple dimensions, so that different stabilizer pads may have different thicknesses while having a constant outer perimeter size. In an exemplary implementation, where pockets are used for the stabilizer regions, there may be, for each of the lateral and medial sides, a first pocket perimeter size for socks in the extra small, small, and medium sizes, and a second pocket size for socks in the large and extra large size. Each pocket could then accommodate stabilizer pads of varying thicknesses.

Reference is now made to FIG. 9C, where a generally reniform lateral stabilizer pad for a human foot is indicated by the reference numeral 920. The lateral stabilizer pad 920 is shaped to, when positioned adjacent a forward lateral region of the rearfoot of a correspondingly sized human foot (e.g. by insertion into the correspondingly shaped pocket defining a lateral stabilizer region 520, as shown in FIG. 6), extend from a position on the foot posterior to the fibular malleolus 46 and anterior to the Achilles tendon 50, curve around the fibular malleolus 46, and extend across a lower lateral part of the talus 18 and an upper lateral part of the calcaneous 20, with a lateral malleolal concavity 932 defined in an upper edge of the lateral stabilizer pad 920 to accommodate the fibular malleolus 46.

Referring now to FIG. 9D, a generally reniform medial stabilizer pad for a human foot is shown generally at 924. The medial stabilizer pad 924 is shaped to, when positioned adjacent a medial part of the foot consisting of a forward medial region of the rearfoot and a rearward medial region of the midfoot (e.g. by insertion into the correspondingly shaped pocket defining a medial stabilizer region 524, as shown in FIG. 7), extend from a position on the foot posterior to the tibial malleolus 48 and anterior to the Achilles tendon 50, curve around the tibial malleolus 48, and extend across a lower medial part of the talus 18 and an upper medial part of the calcaneous 20 to terminate at the proximal aspect of the navicular bone 32, with a medial malleolal concavity 930 defined in an upper edge of the medial stabilizer pad 924 to accommodate the tibial malleolus 48.

FIG. 9E is a rear view of a skeletal human foot, showing the positioning of the medial stabilizer pad 924 and the lateral stabilizer pad 920 relative to the bones therein.

Figure 9F:
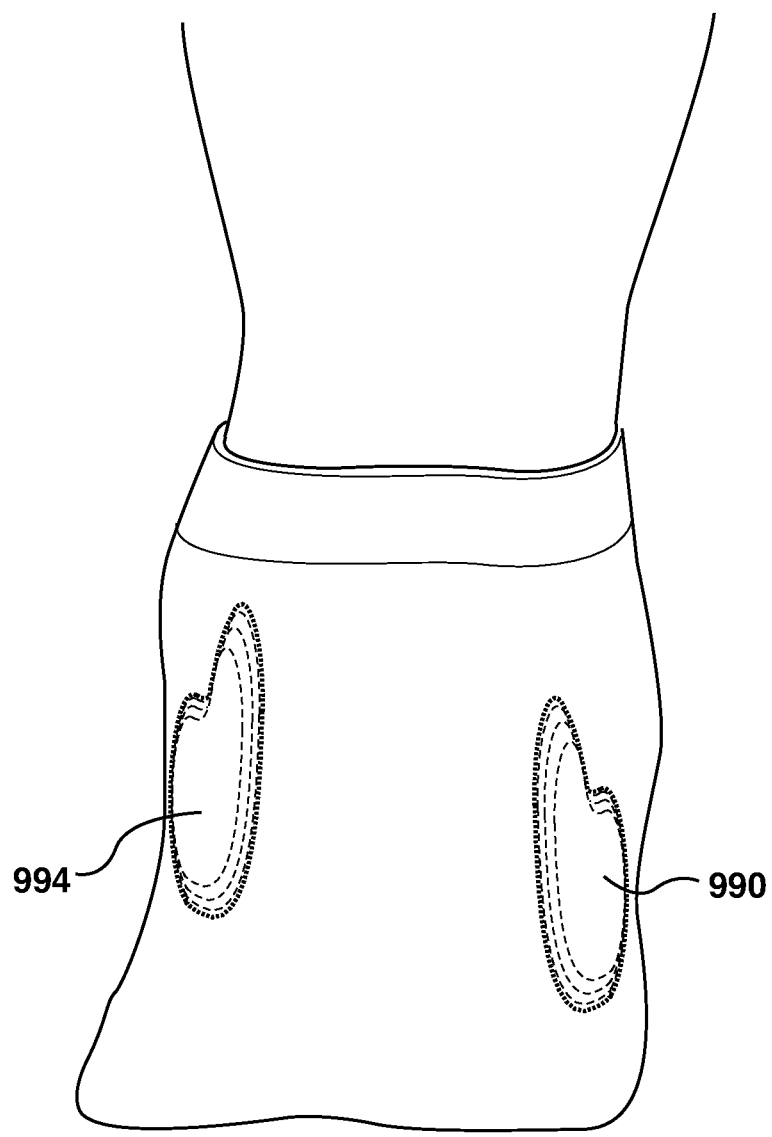
FIG. 9F is a rear view of a second modified embodiment of the foot stabilizer sock of FIG. 5, with a human right foot inside thereof.

In addition, as shown in FIG. 9F, the medial stabilizer region and lateral stabilizer region may comprise portions of the sock having material that is substantially thickened, relative to the surrounding material, to form protrusions 994, 990 that define the medial stabilizer region and lateral stabilizer region.

The first foot stabilizer sock 500 shown in FIGS. 5 to 8, and the pads 920, 924, are intended for use with a low-top running shoe (not shown); hence the foot stabilizer sock 500 may be considered a running sock 500. Other embodiments of stabilizer socks for use with other types of footwear are now described.

Figure 10:
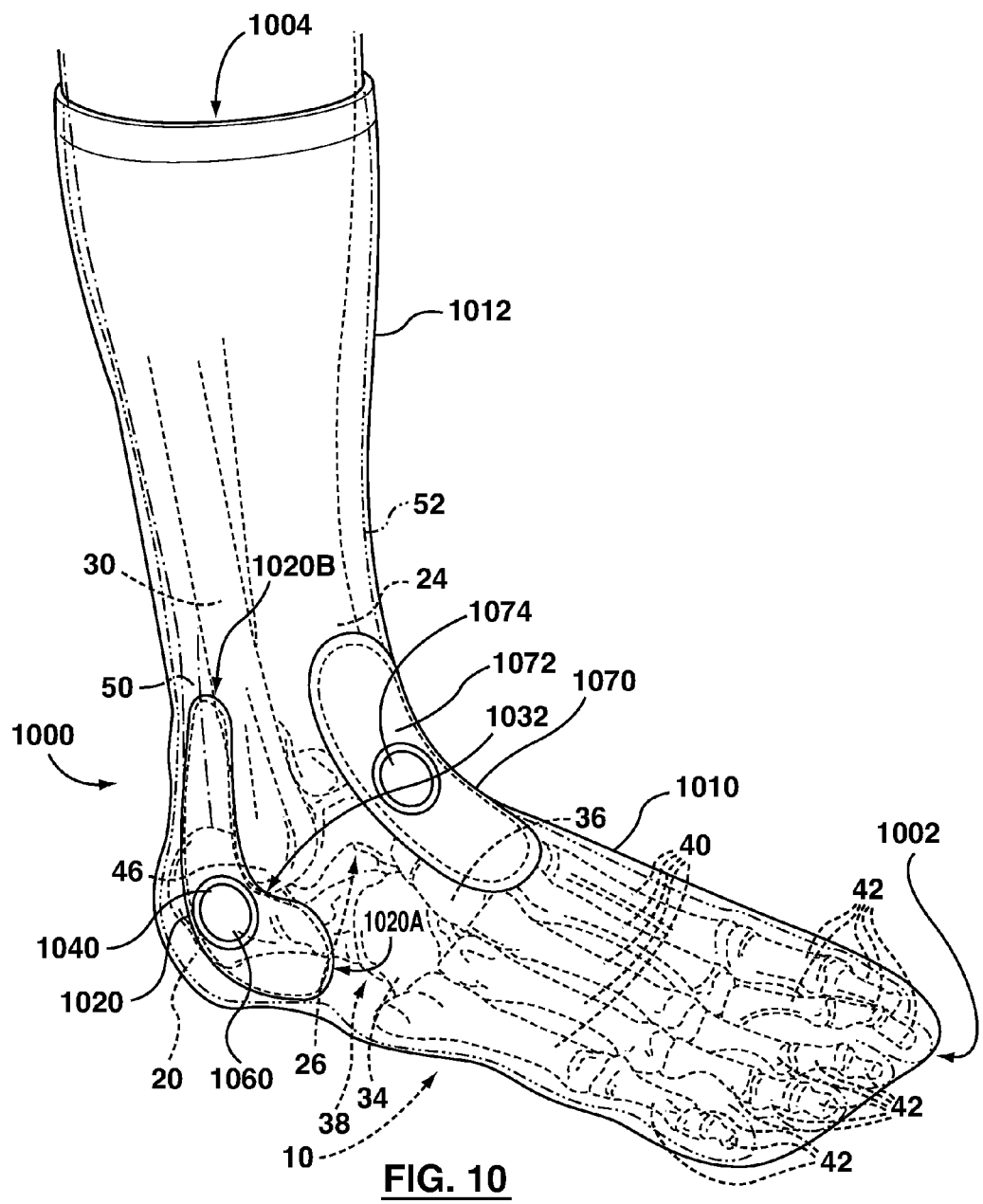
FIG. 10 is a is a perspective view of a second exemplary embodiment of a foot stabilizer sock, according to an aspect of the present invention; with a human right foot inside thereof.

Referring now to FIG. 10, a second exemplary foot stabilizer sock 1000 is shown on a human lower leg 52 including a foot 10. The second foot stabilizer sock 1000 is similar to the first foot stabilizer sock 500 shown in FIGS. 5 to 8, and as such corresponding reference numerals are used to refer to corresponding features, except beginning with the number "10" instead of "5". While the first foot stabilizer sock 500 ended at the ankle, the second foot stabilizer sock 1000 also includes a leg section 1012 extending from the foot section 1010 and corresponding at least to the lower portions of the tibia 24 and fibula 30, and terminating at an open foot-insertion end 1004. As such, the second foot stabilizer sock 1000 is suitable for use with shoes or boots that include an ankle portion, such as hiking, tactical or combat boots, or high-top athletic shoes. The foot stabilizer sock may be particularly advantageously used with skates, such as ice skates or in-line wheeled skates.

With shoes or boots having an ankle portion, in addition to the recessed regions 46A, 48A immediately below the fibular malleolus 46 and the tibial malleolus 48, respectively, there can also be additional gaps between the human ankle and the ankle portion of the footwear in the area adjacent the lower posterior part of the fibula 30, posterior to the fibular malleolus 46 and anterior to the Achilles tendon 50, and in the area adjacent the lower posterior part of the tibia 24, posterior to the tibial malleolus 48 and anterior to the Achilles tendon 50.

Figure 11:
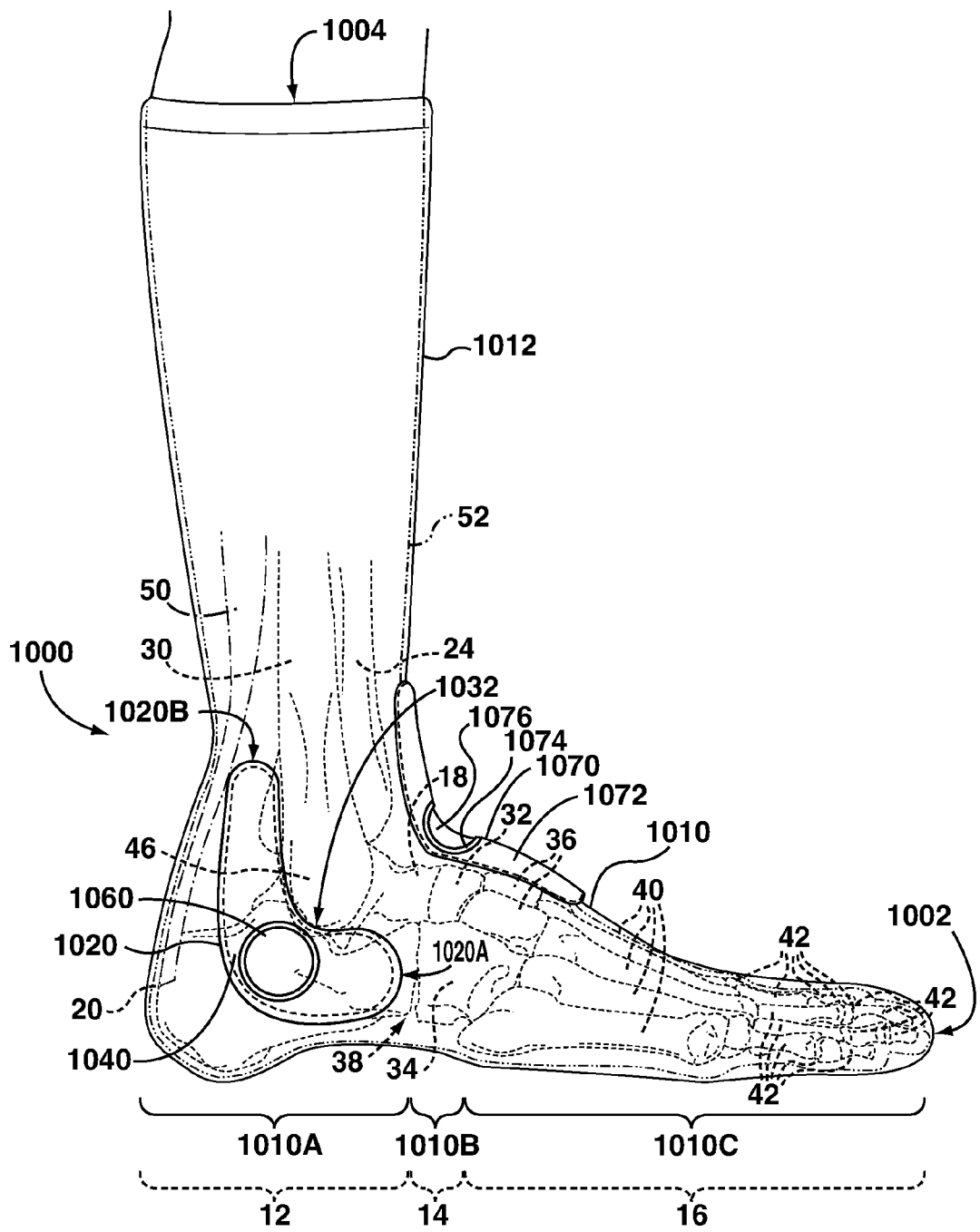
FIG. 11 is a lateral view of the foot stabilizer sock of FIG. 10.
Figure 12:
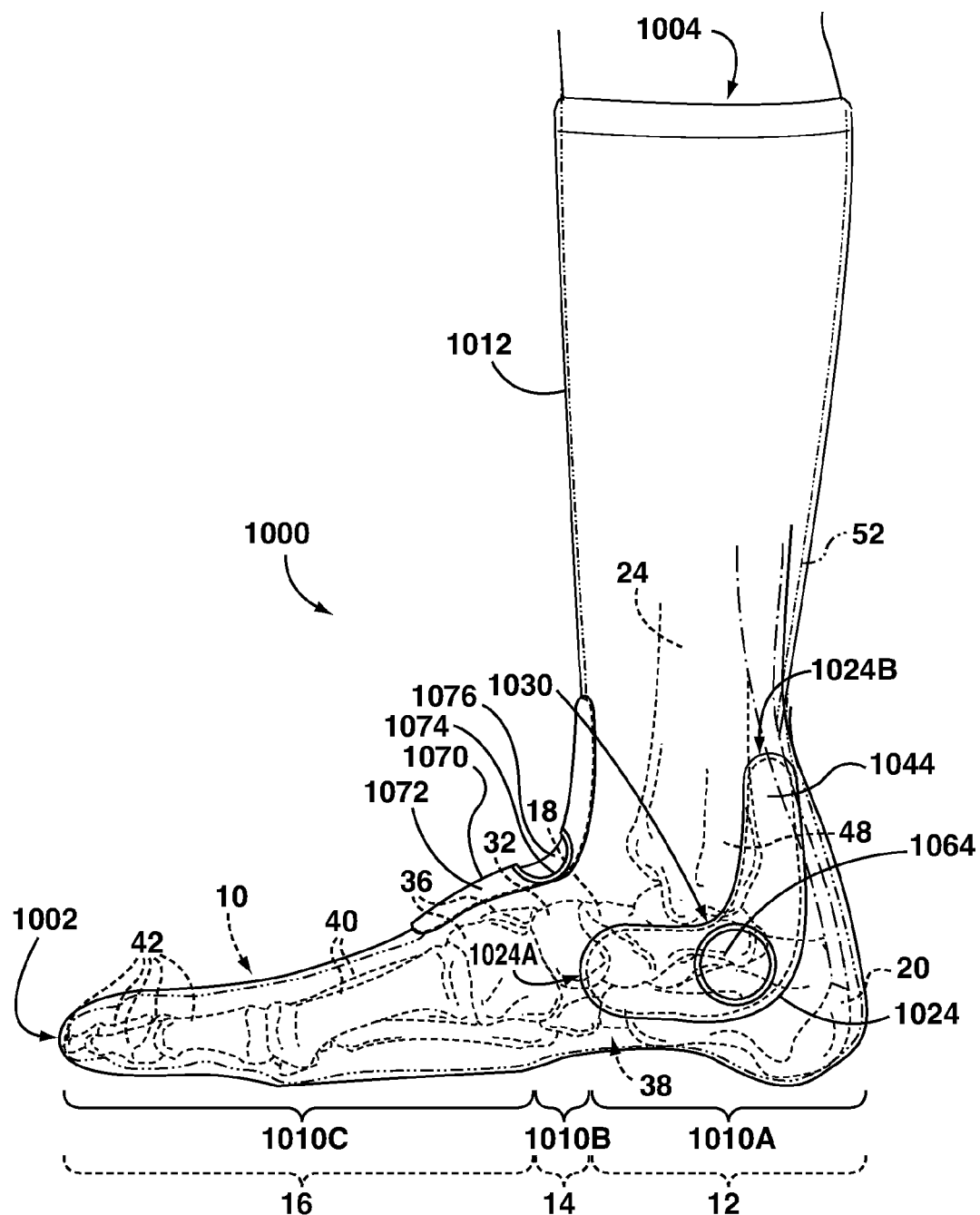
FIG. 12 is a medial view of the foot stabilizer sock of FIG. 10.

Accordingly, in the second foot stabilizer sock 1000, as best seen in FIG. 12 the medial stabilizer region 1024 has an elongate generally reniform shape, and extends downwardly from a position on the rearfoot portion 1010A corresponding to a medial position on the foot 10 posterior to the tibia 24, anterior to the Achilles tendon 50, along an area of the leg section 1012 corresponding to a lower posterior part of the tibia 24, curving beneath the tibial malleolus 48 to define the medial malleolal concavity 1030, and then extending forwardly across a part of the rearfoot portion 1010A corresponding to a lower medial part of the talus 18 and an upper medial part of the calcaneous 20, to terminate at a position on the midfoot portion 1010B corresponding to the navicular bone 32. Similarly, in the second foot stabilizer sock 1000, as best seen in FIG. 11 the lateral stabilizer region 1020 has an elongate generally reniform shape, and extends downwardly from a position on the rearfoot portion 1010A corresponding to a lateral position on the foot 10 posterior to the fibula 30, anterior to the Achilles tendon, along an area of the leg section 1012 corresponding to a lower posterior part of the fibula 30, curving beneath the fibular malleolus 48 to define the fibular malleolal concavity 1032, and extending forwardly across a lower part of the rearfoot portion 1010A corresponding to a lower lateral part of the talus 18 and an upper lateral part of the calcaneous 20. As with the first foot stabilizer sock 500, the medial stabilizer region 1024 has a first end 1024A pointing generally towards the closed toe end 1002 of the foot stabilizer sock 1000, and a second end 1024B pointing generally toward the open foot-insertion end of the foot stabilizer sock 1000, and the lateral stabilizer region 1020 has a first end 1020A pointing generally towards the closed toe end 1002 of the foot stabilizer sock 1000, and a second end 1020B pointing toward the open foot-insertion end of the foot stabilizer sock 1000.

The second foot stabilizer sock 1000 also includes a lace bite protector region 1070 extending along the front surface of the sock 1000 from the posterior upper surface of the foot portion 1010 to the lower anterior surface of the leg portion 1012. More particularly, the lace bite protector region 1070 extends from a position on the forefoot portion 1010C corresponding to the posterior ends of the inner metatarsal bones 40, across the upper part of the midfoot portion 1010B corresponding to at least the inner cuneiform bones 36 and the navicular bone 32, and then upwardly along the lower front of the leg section 1012, corresponding to the lower front of the tibia 24 and fibula 30. In the illustrated embodiment, the lace bite protector region 1070 comprises a pocket 1072 having a stretchable aperture 1074 permitting a suitable pad 1076 to be inserted into the pocket 1072 to provide cushioning so as to prevent tight laces on a piece of footwear, such as an ice skate or in-line wheeled skate, from biting into a user's foot, and also to increase stability by providing an interface between the top of the foot 10 and the lace portion of the footwear. An exemplary lace bite protector pad will be described in greater detail below.

Figure 13:
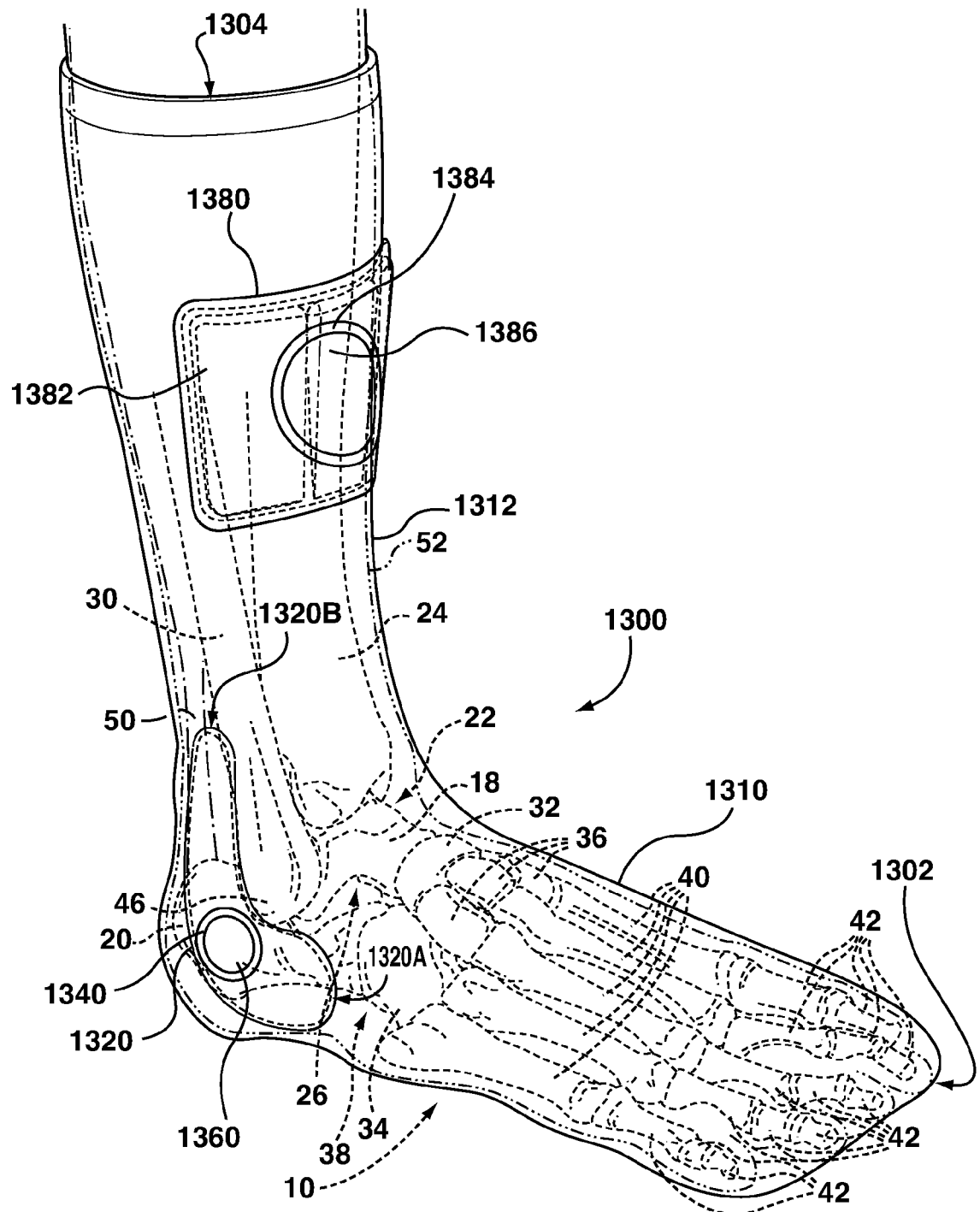
FIG. 13 is a is a perspective view of a third exemplary embodiment of a foot stabilizer sock, according to an aspect of the present invention; with a human right foot inside thereof.
Figure 14:
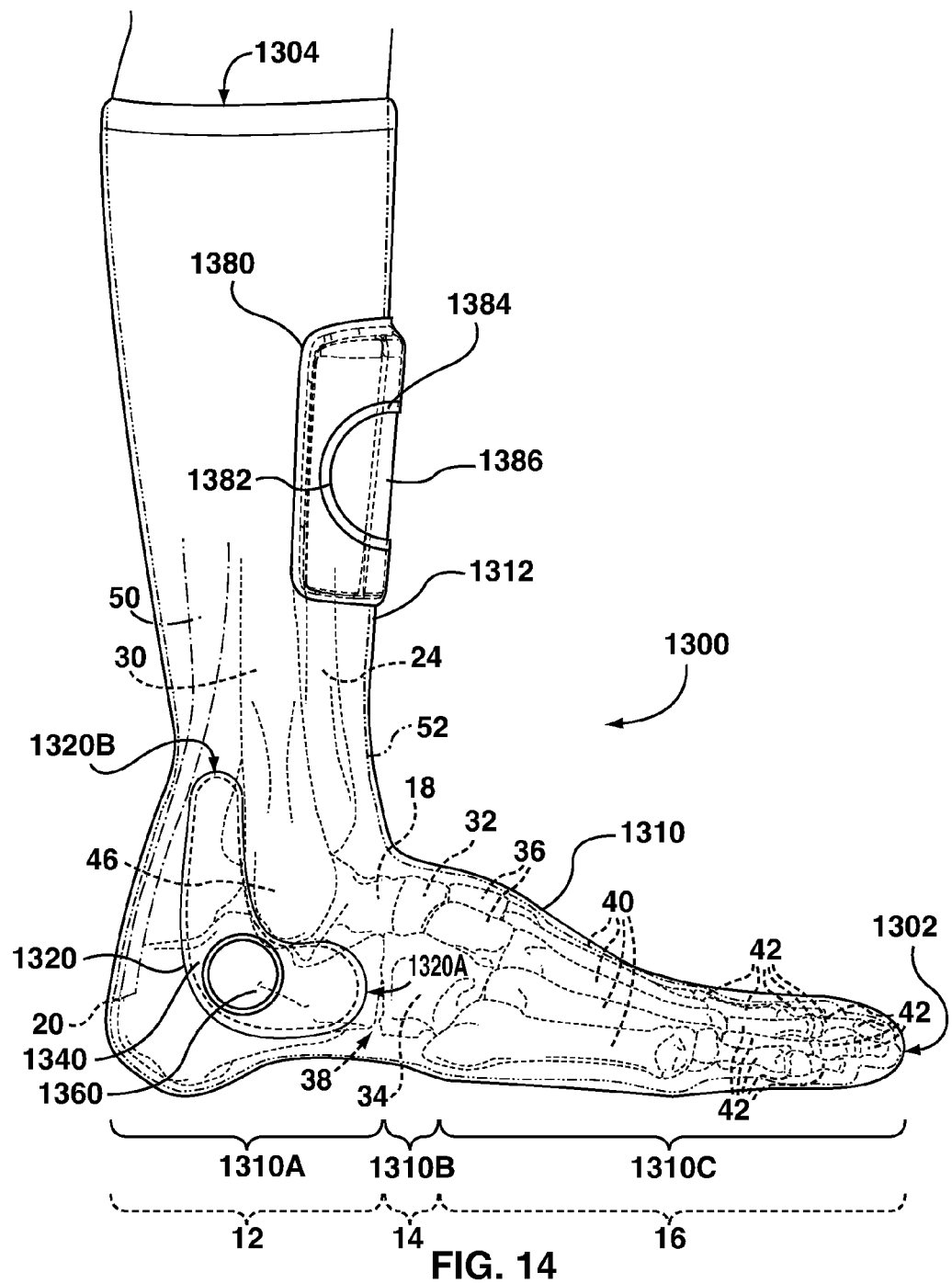
FIG. 14 is a lateral view of the foot stabilizer sock of FIG. 13.
Figure 15:
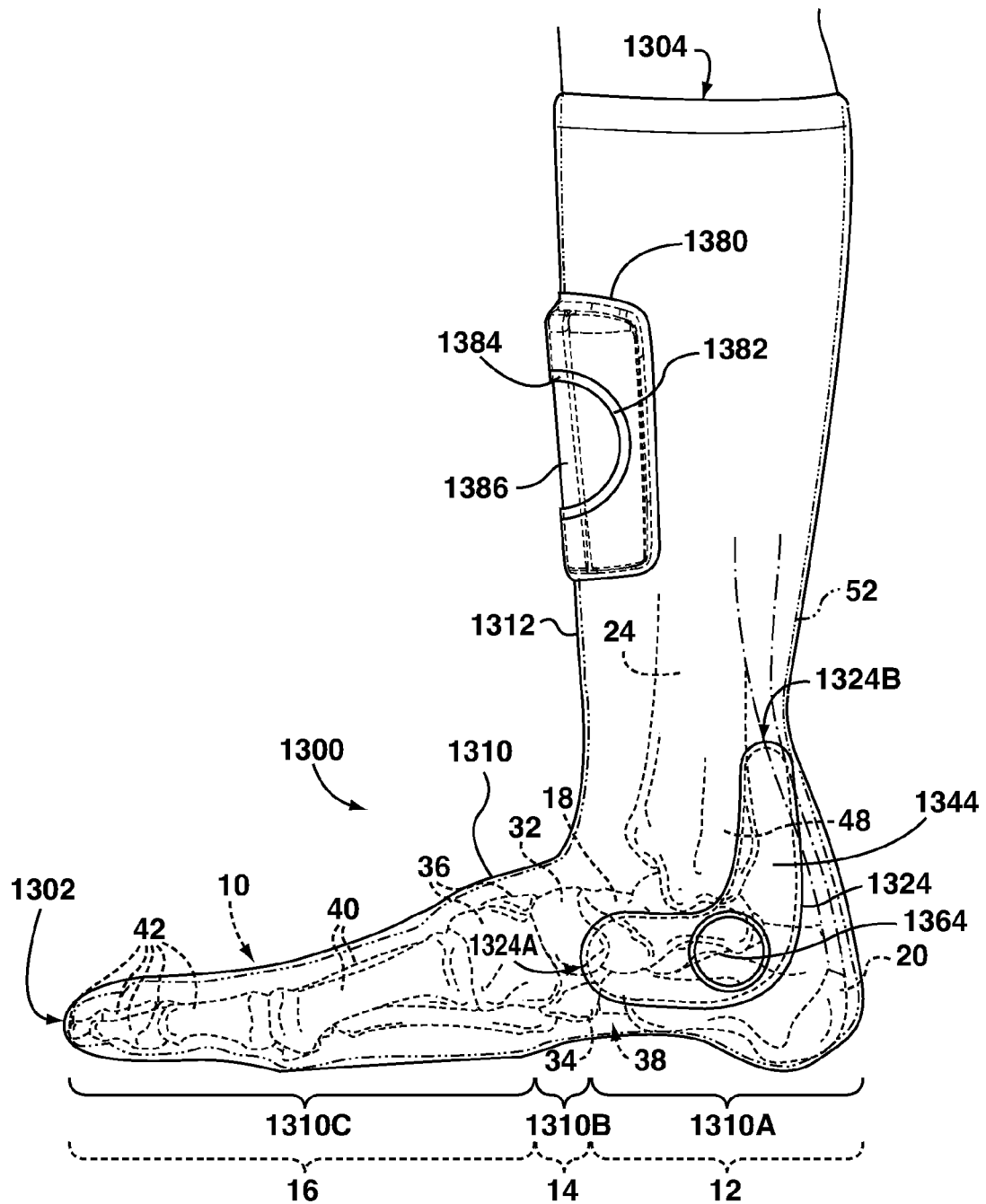
FIG. 15 is a medial view of the foot stabilizer sock of FIG. 13.

Reference is now made to FIGS. 13 to 15, where a third embodiment of a foot stabilizer sock 1300 is shown on a human lower leg 52, including the foot 10. The third foot stabilizer sock 1300 is similar to the second foot stabilizer sock 1000 shown in FIGS. 10 to 12, and as such corresponding reference numerals are used to refer to corresponding features, except beginning with the number "13" instead of "10". Like the second foot stabilizer sock 1000, the third foot stabilizer sock 1300 includes a leg section 1312 extending from the foot section 1310 and corresponding at least to the lower portions of the tibia 24 and fibula 30 and is therefore suitable for use with shoes or boots that include an ankle portion. The lateral stabilizer region 1320 and the medial stabilizer region 1324 of the third embodiment of the stabilizer sock 1300 have the same shape, position and orientation on the sock 1300 as do the lateral stabilizer region 1020 and the medial stabilizer region 1024 of the second embodiment of the stabilizer 1000.

The third embodiment of the stabilizer sock 1300 includes a boot bang protector region 1380 positioned on the leg section 1312 of the stabilizer sock 1300. In certain sporting activities where the user wears boots constructed of hard plastic, such as skiing, the user's shins, and in particular the anterior margin of the tibia 24, can collide with the inside of the boot, potentially causing injury. The boot bang protector region 1380 is positioned to cushion the user's legs against such impact. In the illustrated embodiment, the boot bang protector region 1380 comprises a pocket 1382 having a stretchable aperture 1384 permitting a suitable pad 1386 to be inserted into the pocket 1382 to provide cushioning. An exemplary boot bang protector pad will be described in greater detail below.

Figure 16A:
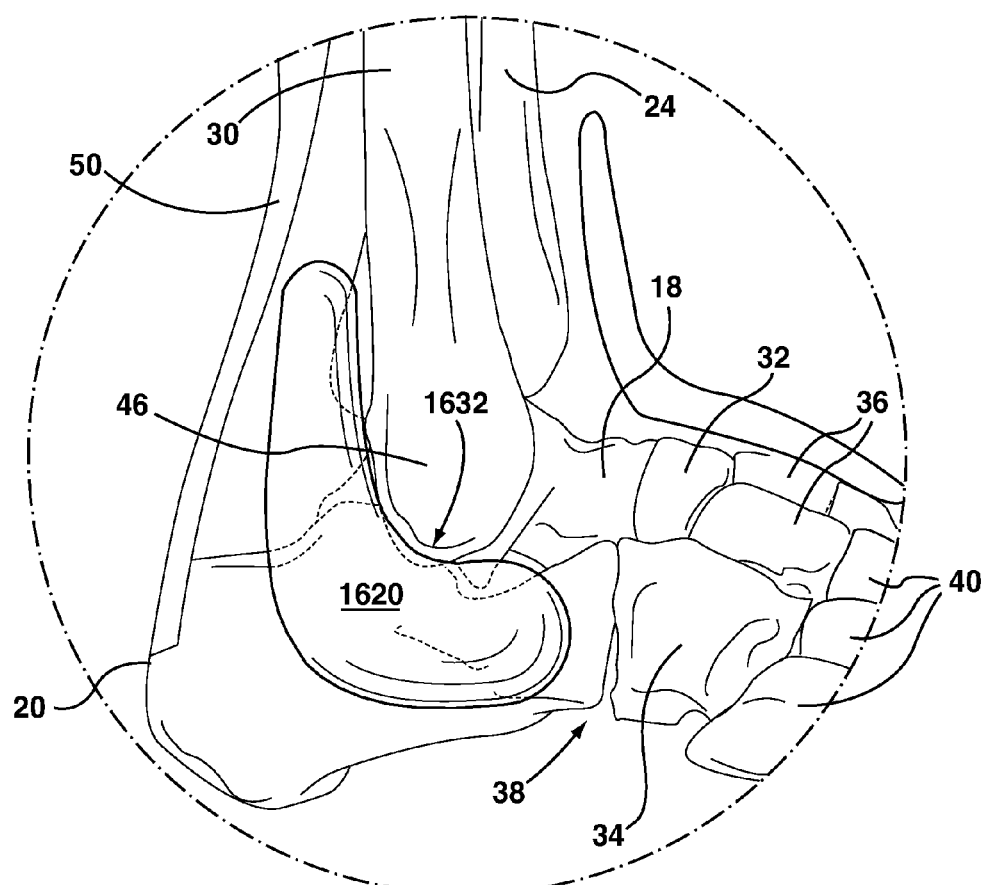
FIG. 16A shows a second exemplary lateral stabilizer pad, positioned relative to the lateral side of a skeletal human right foot.
Figure 16B:
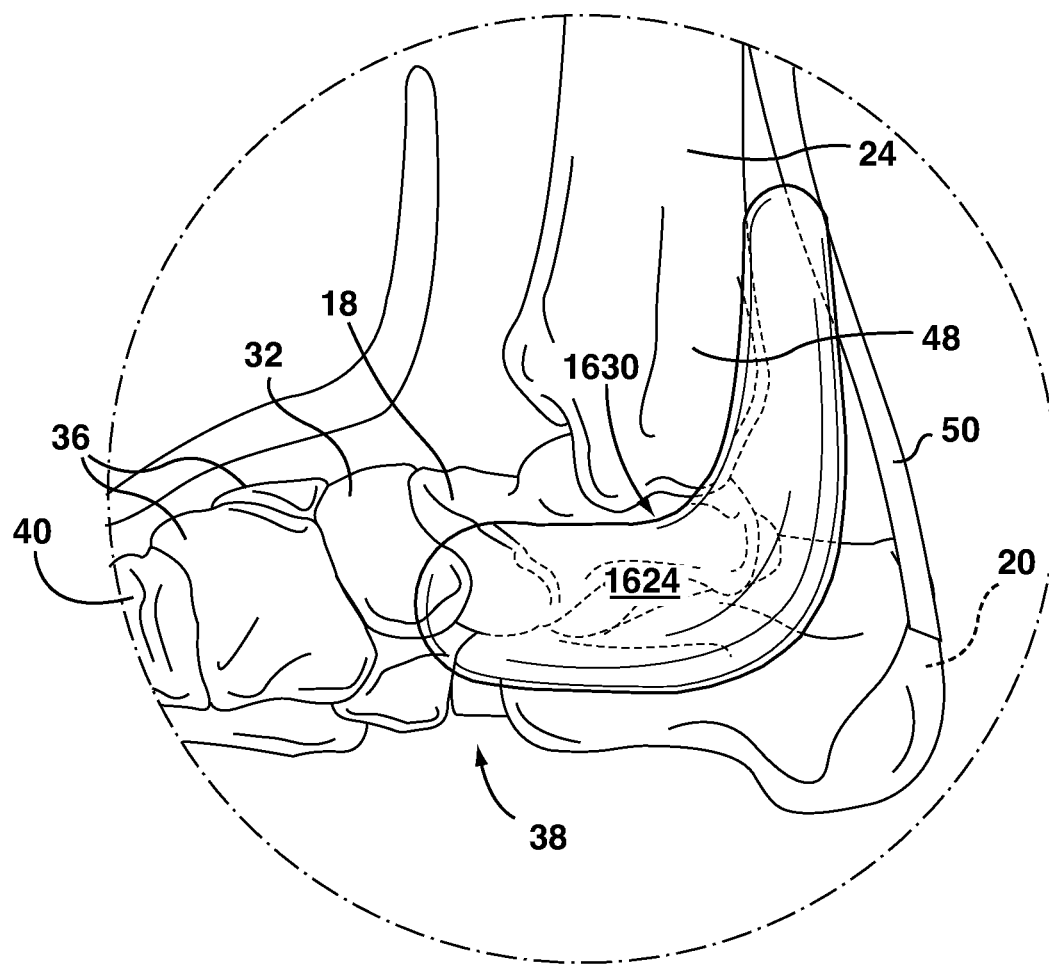
FIG. 16B shows a second exemplary medial stabilizer pad, positioned relative to the medial side of a skeletal human right foot.

FIGS. 16A and 16B show stabilizer pads for use with the second and third embodiments 1000, 1300 of stabilizer socks according to aspects of the present invention. In particular, FIG. 16A shows a lateral stabilizer pad 1620, and FIG. 16B shows a medial stabilizer pad 1624.

Referring to FIG. 16A, the lateral stabilizer pad 1620 is shaped to, when positioned adjacent a forward lateral region of the rearfoot of a correspondingly sized human foot (e.g. by insertion into the pocket defining a lateral stabilizer region 1020, 1320 as shown in FIGS. 11 and 14, respectively) extend downwardly from a lateral position posterior to the fibula 30, anterior to the Achilles tendon, along the lower posterior part of the fibula 30, curving beneath the fibular malleolus 48 to define the fibular malleolal concavity 1032, and extending forwardly across a lower part of the rearfoot portion 1010A corresponding to a lower lateral part of the talus 18 and an upper lateral part of the calcaneous 20.

Now referring to FIG. 16B, the medial stabilizer pad 1624 is shaped to, when positioned adjacent a forward medial region of the rearfoot of a correspondingly sized human foot (e.g. by insertion into the pocket defining a medial stabilizer region 1024, 1324 as shown in FIGS. 12 and 15, respectively), extend downwardly from a medial position posterior to the tibia 24, anterior to the Achilles tendon 50, along the lower posterior part of the tibia 24, curving beneath the tibial malleolus 48 to define the medial malleolal concavity 1630, and then extend forwardly across a lower part of the rearfoot portion 1010A and midfoot portion 1010B corresponding to the lower medial part of the talus 18 and the upper medial part of the calcaneous 20, to terminate at the proximal aspect of the navicular bone 32.

Figure 16C:
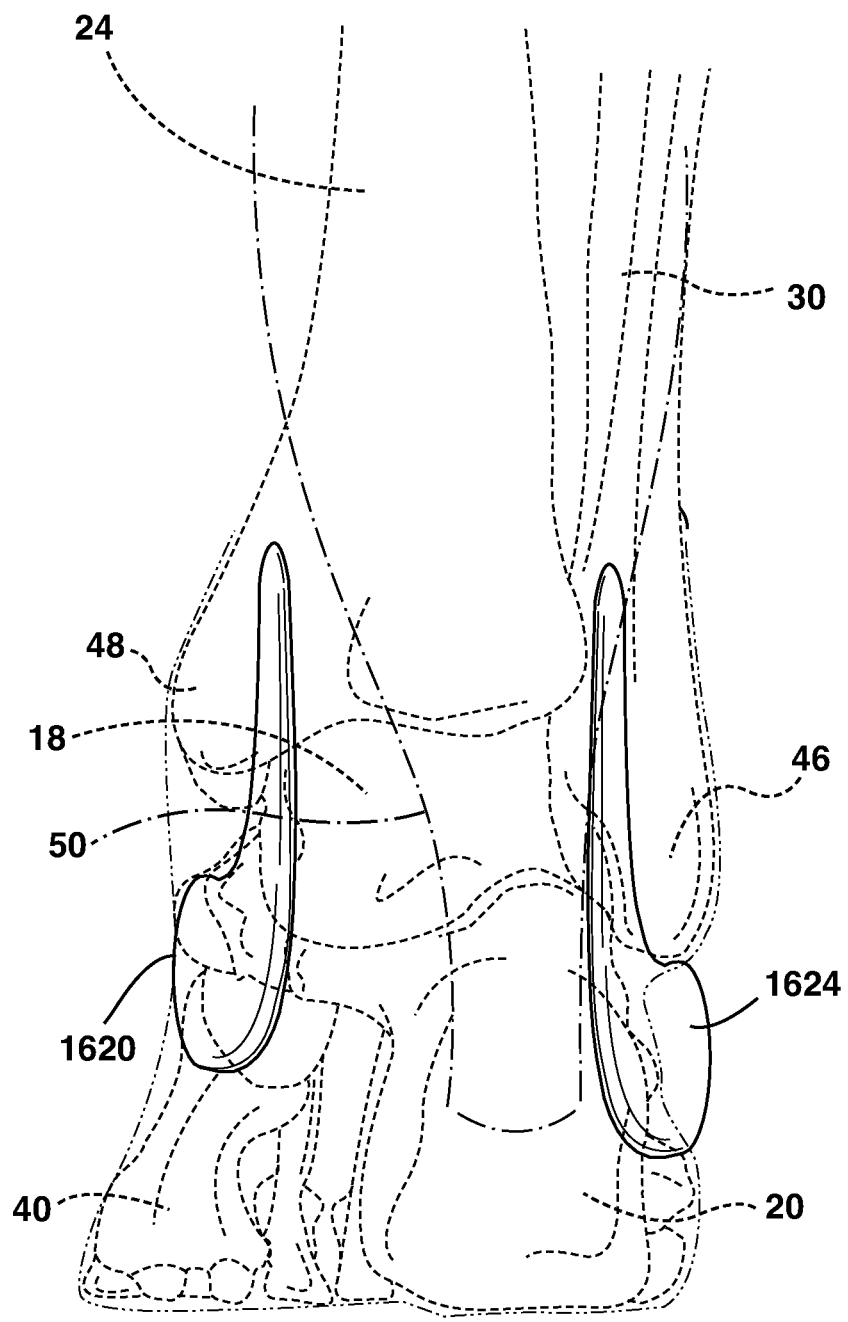
FIG. 16C shows the lateral stabilizer pad of FIG. 16A and the medial stabilizer pad of FIG. 16B, positioned relative to the rear of a skeletal human foot.

FIG. 16C is a rear view of a skeletal human foot, showing the positioning of the medial stabilizer pad 1624 and the lateral stabilizer pad 1620.

While the medial stabilizer regions 1024, 1324, lateral stabilizer regions 1020, 1620, lace bite protector region 1070 and boot bang protector region 1380 have been depicted in FIGS. 10 to 12 and 13 to 16 as pockets, it will be appreciated that these regions may also be formed by one of hook or loop attachment fabric, or by thickened material of the sock defining protrusions, as described above.

As a matter of brevity, only right foot socks have been illustrated in detail in the above-described figures; it will be appreciated that left foot socks according to aspects of the present invention will be substantially identical to right foot socks, but arranged as a mirror image thereof.

FIGS. 9C and 9D and FIGS. 16B and 16C show embodiments of lateral stabilizer pads 920, 1620 and medial stabilizer pads 924, 1624, respectively, which are preferred from an anatomical perspective. Specifically, it will be observed that the medial stabilizer pads 924, 1624 have a more elongate lower portion (i.e. extend further toward the toes when properly positioned) than the lateral stabilizer pads 920, 1620. This difference in shape is also reflected in the medial stabilizer regions 524, 994, 1024, 1324 and the lateral stabilizer regions 520, 990, 1020, 1320. While this difference in shape is preferable from an anatomical perspective, it is presently preferred, from a manufacturing simplification perspective, to use identically shaped pads as both medial stabilizer pads and lateral stabilizer pads. Although this approach is less preferred from an anatomical perspective, it is still sufficient from an anatomical perspective and has the benefit of reducing the number of different types of stabilizer pads that must be manufactured.

Aspects of the present invention also provide for a kit for assembling a stabilizer sock. Such a kit would include at least one sock, and preferably two socks, which include a medial stabilizer region and a lateral stabilizer region as described herein, such as the socks 500, 1000 1300. A kit including two socks will preferably include one right foot sock and one left foot sock.

As will be appreciated, different sizes of foot stabilizer socks according to aspects of the present invention may be used for different sizes of feet. In addition to the socks, a kit according to an aspect of the present invention would also include a plurality of stabilizer pads, such as the pads 920, 924, 1620, 1624, of various thicknesses. The pads are provided in various thicknesses to allow a user to select a pad having the thickness best suited to the user's foot and the outer footwear with which the sock will be worn. Each stabilizer pad in the kit will have a perimeter shape matching a perimeter shape of at least one of the medial stabilizer region and the lateral stabilizer region and will be securable at the corresponding medial stabilizer region and/or lateral stabilizer region, for example by insertion into a pocket. In one embodiment, differently shaped medial stabilizer pads and lateral stabilizer pads are provided. In such an embodiment, each medial stabilizer pad has a perimeter shape matching the perimeter shape of the corresponding medial stabilizer region, and each lateral stabilizer pad has a perimeter shape matching the perimeter shape of the corresponding lateral stabilizer region. In another embodiment, the kit includes pads of a single general shape, which may be used as both medial and lateral stabilizer pads.

Such a kit would also include instructions for selecting at least one of the medial stabilizer pads and securing each selected one of the medial stabilizer pads at a corresponding medial stabilizer region, and for selecting at least one of the lateral stabilizer pads and securing each selected one of the lateral stabilizer pads to a corresponding lateral stabilizer region. For example, the instructions may provide for the installation of two medial or lateral stabilizer pads inside a single pocket, to provide thicker padding than a single pad. The instructions can optionally form part of the packaging in which the kit is sold.

Figure 17:
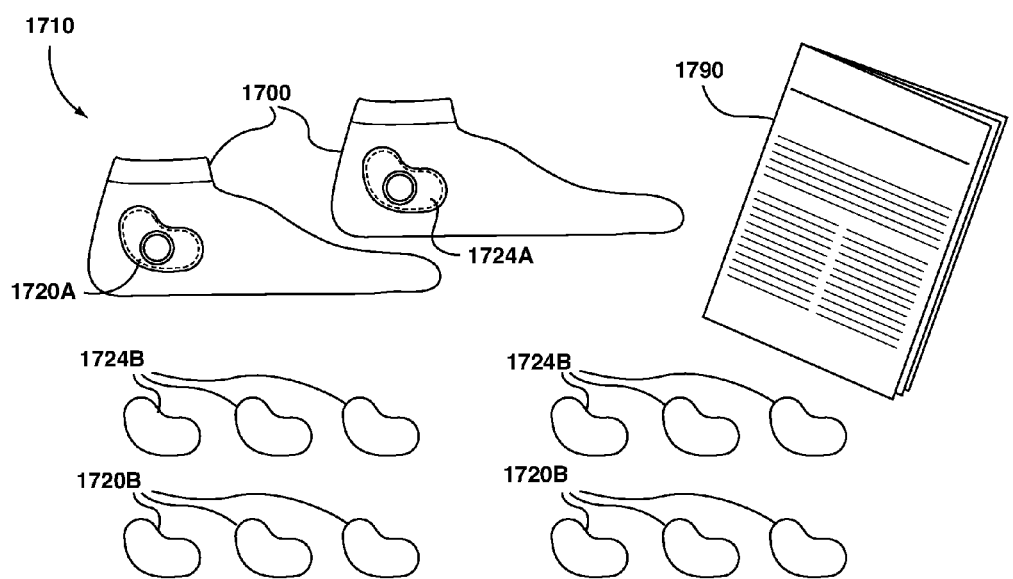
FIG. 17 shows a first exemplary kit, according to an aspect of the present invention.
Figure 18:
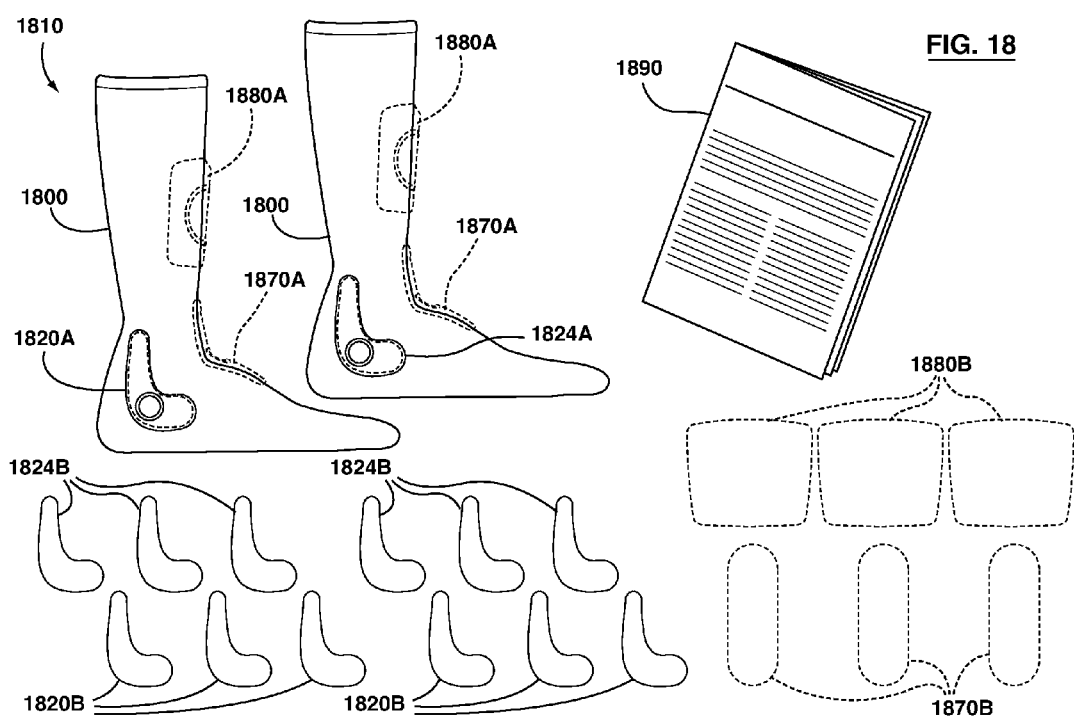
FIG. 18 shows a second exemplary kit, according to an aspect of the present invention.

With reference now to FIG. 17, an exemplary kit is shown generally at 1710. The kit 1710 includes two socks 1700 similar in construction to the sock 500, each having a medial stabilizer region 1720A and a lateral stabilizer region 1724A, and also includes a plurality of correspondingly shaped medial stabilizer pads 1720B and lateral stabilizer pads 1724B, similar to the medial and lateral stabilizer pads 920 and 924, respectively. The kit 1710 also includes a set of instructions 1790 for selecting and securing the medial stabilizer pads 1720B and lateral stabilizer pads 1724B. Similarly, FIG. 18 depicts an exemplary kit 1810. The kit 1710 includes two socks 1800, each having a medial stabilizer region 1820A and a lateral stabilizer region 1824A, and also includes a plurality of correspondingly shaped medial stabilizer pads 1720B and lateral stabilizer pads 1724B, similar to the medial and lateral stabilizer pads 1620 and 1624, respectively. In addition, the socks 1810 may include lace bite protector regions 1870A, similar to the lace bite protector region 1070A, or boot bang protector regions 1880A similar to the boot bang protector region 1380, or both, and the kit 1810 includes a plurality of lace bite protector pads 1870B of different thicknesses, a plurality of boot bang protector pads 1880B of different thicknesses, or both. Like the kit 1710, the kit 1810 also includes a set of instructions 1890 for selecting and securing the medial stabilizer pads 1820B and lateral stabilizer pads 1824B.

Figures 19A, 19B:
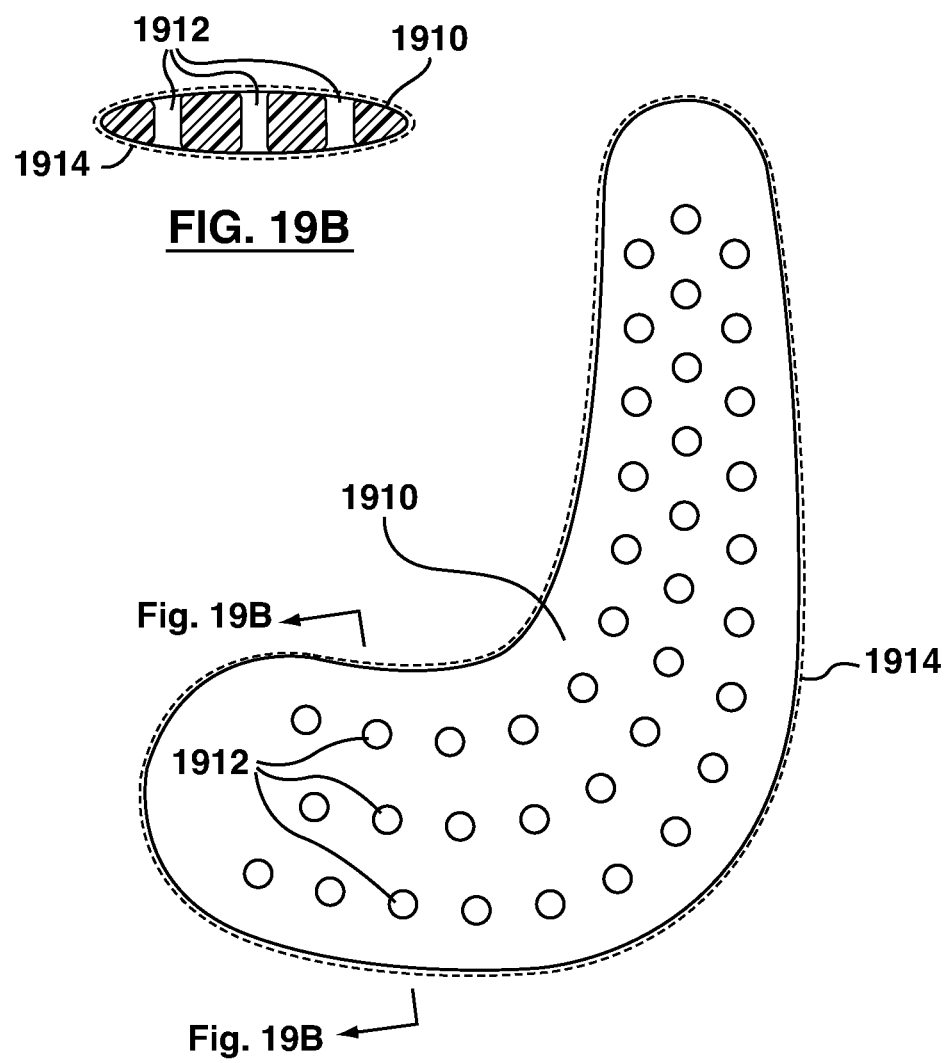
FIG. 19A shows construction of an exemplary stabilizer pad, according to an aspect of the present invention.
FIG. 19B is a cross-sectional view taken along the line 19B-19B in FIG. 19A.

Lateral stabilizer pads such as the pads 520, 920, 1620 and medial stabilizer pads such as the pads 524, 924, 1624 may be formed from a variety of suitable materials. For example, the pads 920, 924 may be formed from a material comprising silicone, from foam (such as memory foam), or the pads 920, 924 may comprise a gel or a gel-filled enclosure. FIGS. 19A and 19B show an exemplary pad 1910 formed from a suitable gel material. The pad 1910 has a plurality of apertures 1912 defined therethrough to improve breathability, and may optionally be disposed within a covering of breathable fabric 1914.

Foot stabilizer socks, such as the socks 500, 1000 and 1300, may, in addition to the inventive lateral and medial stabilizer regions and pads, include thickened fabric or other material to provide cushioning and durability at the rearfoot and forefoot, arch support at the midfoot, and fabric with increased breathability on the upper surface of the foot section. Foot stabilizer socks according to an aspect of the present invention may be made from fabric comprising a suitable Nylon/polyester/spandex blend, such as 77% Nylon, 20% polyester and 3% spandex.

Figure 20:
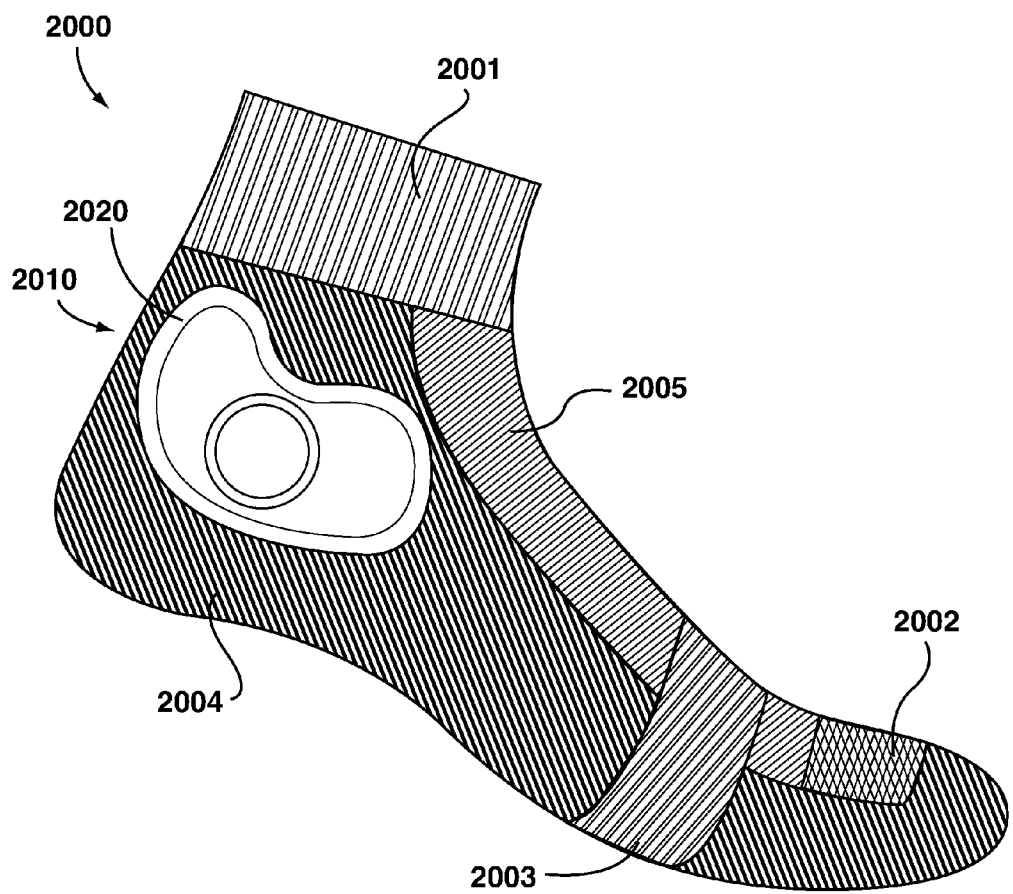
FIG. 20 is a side view of an exemplary running sock according to an aspect of the present invention.

With reference now to FIG. 20, an exemplary construction of a running sock for use with a running shoe is shown generally at 2000 and comprises a foot section 2010. The exemplary running sock 2000 includes both lateral and medial stabilizer regions as described above; only the lateral stabilizer region 2020 is shown in FIG. 20, taking the form of a pocket as described above. Positioning of the lateral and medial stabilizer regions is as described above in respect of FIGS. 5 to 8, and is also described in greater detail below. The exemplary running sock 2000 comprises a cuff part 2001, a toe ventilation part 2002, a fitting band 2003, a foot bottom part 2004 and a foot top part 2005. The cuff part 2001 is made from a 2×1 rib knit, folded over for double thickness, the toe ventilation part 2002 is made from a 1×1 mesh knit, the fitting band 2003 is made from a 2×1 rib knit, the foot bottom part 2004 is made from a cushion knit or terry knit and the foot top part 2005 is made from a flat knit.

Figure 21:
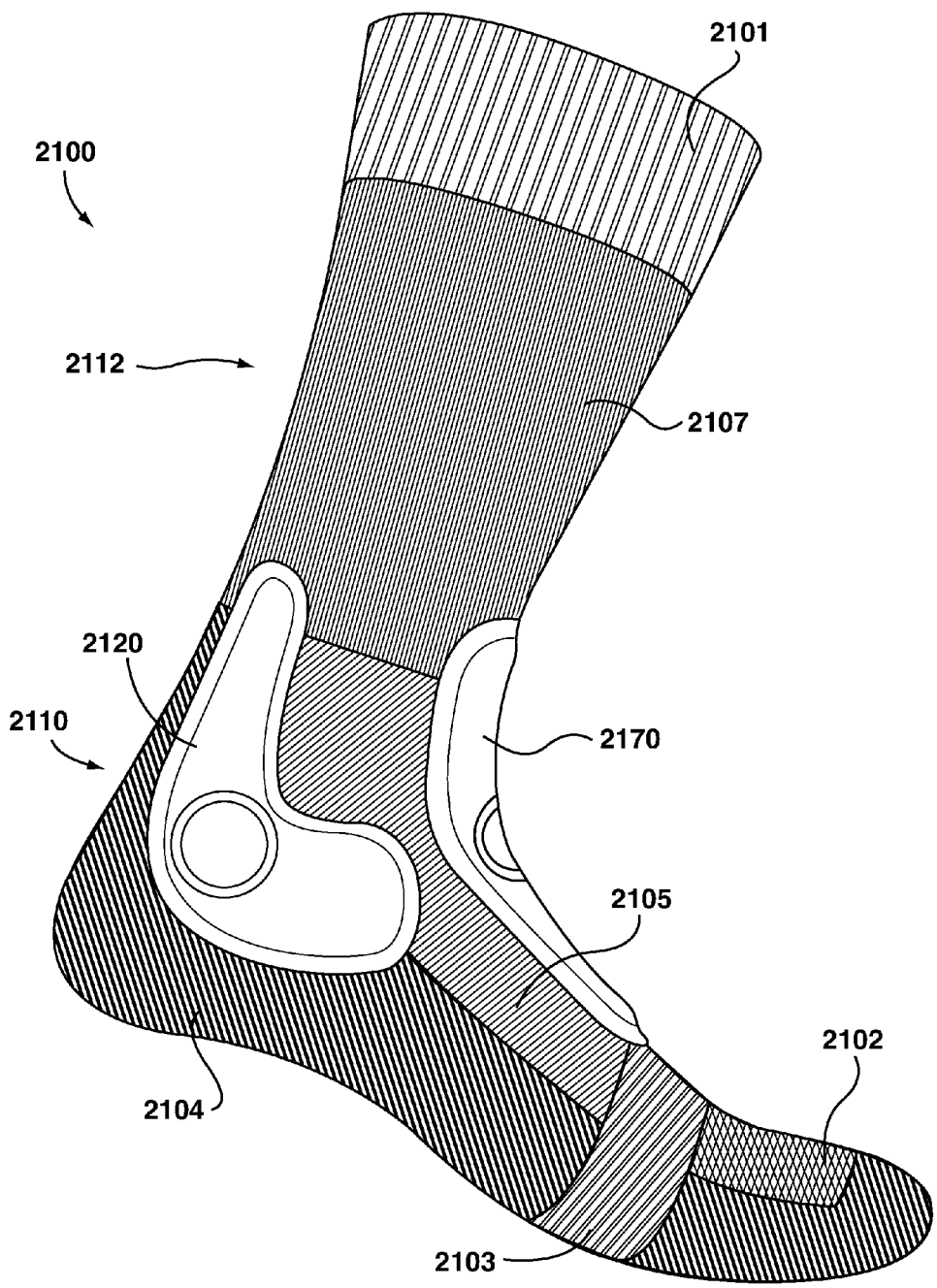
FIG. 21 is a side view of an exemplary skating sock according to an aspect of the present invention.

Reference is now made to FIG. 21, where an exemplary construction of a skating sock for use with a skate (e.g. an ice skate or in-line wheeled skate) is shown generally at 2100 and includes a foot section 2110 and a leg section 2112. Like the exemplary running sock 2000, the exemplary skating sock 2100 includes both lateral and medial stabilizer regions (only the lateral stabilizer region 2120, in the form of a pocket, is shown in FIG. 21). The exemplary skating sock 2100 also includes a lace bite protector pocket 2170. Positioning of the lateral and medial stabilizer regions is as described above in respect of FIGS. 10 to 12 and 16A to 16C and is also described further below. The exemplary hockey sock 2100 comprises a cuff part 2101, a toe ventilation part 2102, a fitting band 2103, a foot bottom part 2104, a foot top part 2105 and a leg part 2107. The cuff part 2101 is made from a 2×1 rib knit, folded over for double thickness, the toe ventilation part 2102 is made from a 1×1 mesh knit, the fitting band 2103 is made from a 2×1 rib knit, the foot bottom part 2104 is made from a cushion knit or terry knit and the foot top part 2105 and leg part 2107 are made from a flat knit.

Figure 22:
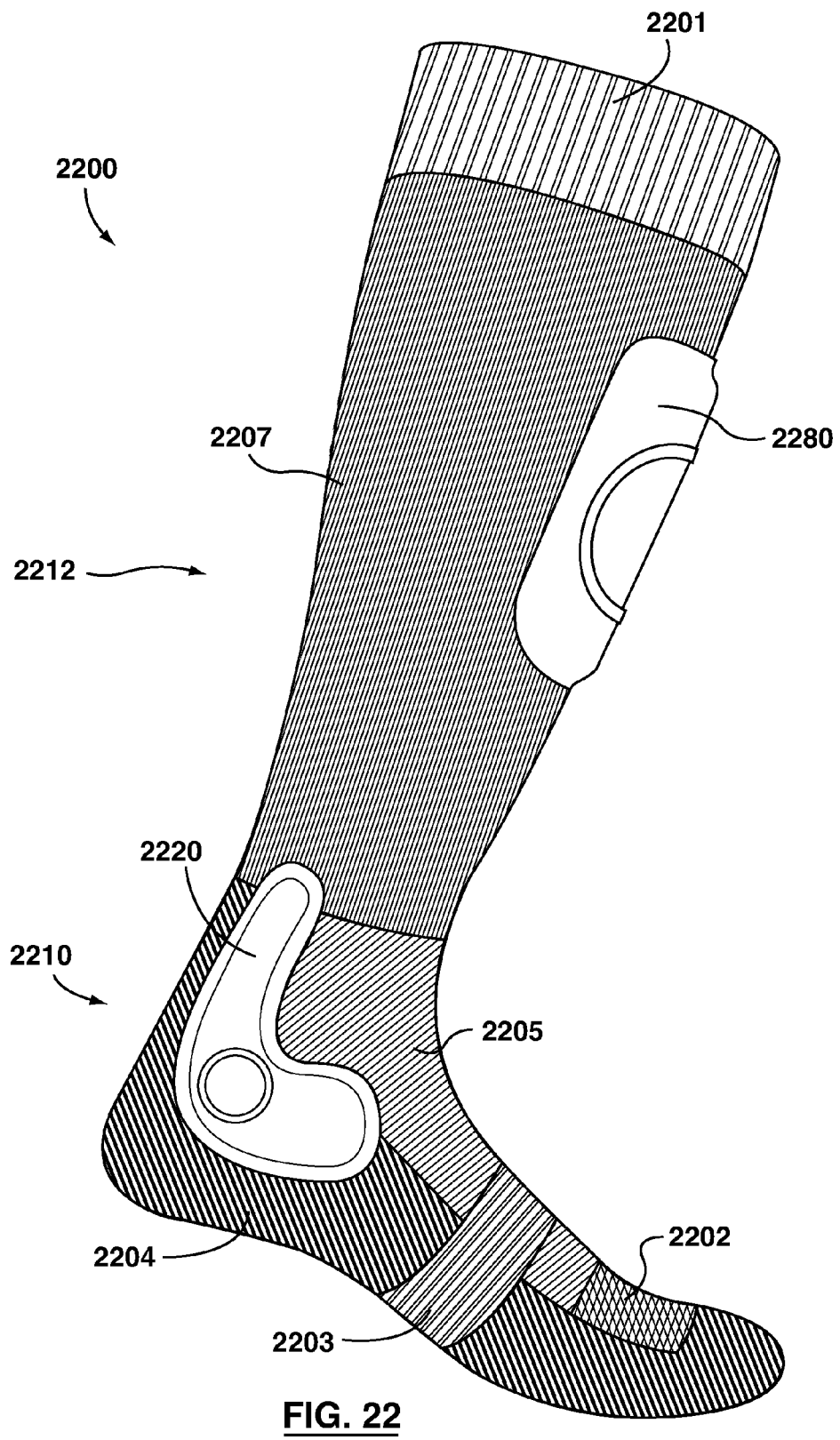
FIG. 22 is a side view of an exemplary skiing sock according to an aspect of the present invention.

FIG. 22 shows an exemplary skiing sock 2200 for use with a ski boot. The skiing sock 2200 and includes a foot section 2110 and a leg section 2112. Like the exemplary socks 2000 and 2100 described above, the exemplary skiing sock 2200 includes both lateral and medial stabilizer regions in the form of pockets (only the lateral stabilizer region 2220 being shown). Similarly to the exemplary hockey sock 2100, the exemplary skiing sock 2200 comprises a cuff part 2201 made from a 2×1 rib knit, folded over for double thickness, a toe ventilation part 2202 made from a 1×1 mesh knit, a fitting band 2203 made from a 2×1 rib knit, a foot bottom part 2204 made from a cushion knit or terry knit, and a foot top part 2205 and leg part 2207 made from a flat knit. Optionally, for increased warmth certain portions of the skiing sock 200, such as the leg part 2207 and the portion of the foot bottom part 2204 immediately forward of the fitting band 2203 and below the toe ventilation part 2202, may be made from wool or a wool blend.

As noted above, stabilizer pads and socks according to aspects of the present invention may be provided in a variety of sizes. In a presently preferred embodiment, medial and lateral stabilizer pads, boot bang protector pads and lace bite protector pads are provided in medium (M), large (L), and extra-large (XL) sizes, with each size being provided in three different thicknesses, for a total of nine different sizes.

FIGS. 23B to 23D show, respectively, a front, side and perspective view of an exemplary stabilizer pad 2300 for a hockey or skiing sock, which may be used as both a medial stabilizer pad and/or a lateral stabilizer pad. A table 2302 containing exemplary height, width and thickness measurements for each size of stabilizer pad 2300 is shown in FIG. 23A. Similarly, FIGS. 24A to 24C show, respectively, a front, side and perspective view of an exemplary stabilizer pad 2400, which may be used as both a medial stabilizer pad and/or a lateral stabilizer pad, with exemplary height, width and thickness measurements for each size of stabilizer pad 2400 shown in the table 2404 in FIG. 24D.

FIGS. 25A to 25C and 26A to 26C show, respectively, exemplary left and right side embodiments of boot bang protector pads 2500, 2600 according to an aspect of the present invention in front, side and perspective views. The tables 2512, 2612 in FIGS. 25D and 26D, respectively, show exemplary height, width and thickness measurements for each size of the boot bang protector pads 2500, 2600.

As can be seen, in the exemplary embodiment each boot bang protector pad 2500, 2600 comprises a monolithic piece of material and includes a lateral pad portion 2502, 2602, a central pad portion 2504, 2604 and a medial pad portion 2506, 2606, separated by living hinges 2508, 2608. The lateral pad portion 2502, 2602 is narrower than the central pad portion 2504, 2604, which in turn is narrower than the medial pad portion 2506, 2606, in each case measured in a direction generally perpendicular to the longitudinal direction of the living hinges 2508, 2608. The living hinges 2508, 2608 allow the boot bang protector pads 2500, 2600 to flex so as to accommodate the shape of the wearer's lower leg. Perforations 2510, 2610 are provided in the lateral pad portion 2502, 2602, central pad portion 2504, 2604 and medial pad portion 2506, 2606

FIGS. 27A to 27D show front, side, perspective and end views, respectively, of an exemplary lace bite protector pad 2700 according to an aspect of the present invention, along with exemplary height, width and thickness measurements for each size. The lace bite protector pad 2700 takes the form of an elongated oval, and includes two spaced-apart, elongate convex projections 2702 defining a concave recess 2704 therebetween. This shape assists in distributing the pressure from the laces across the entire lace bite protector pad 2700 and reducing lace bite perceived by a wearer. Perforations 2710 are provided in the elongate projections 2702. The table 2712 in FIG. 27E shows exemplary height, width and thickness measurements for each size of lace bite protector pad 2700.

It will of course be appreciated that the FIGS. 23A to 27E show only a single exemplary thickness, and that the respective pads may be thicker or thinner than shown, as indicated in the tables.

Figure 28A:
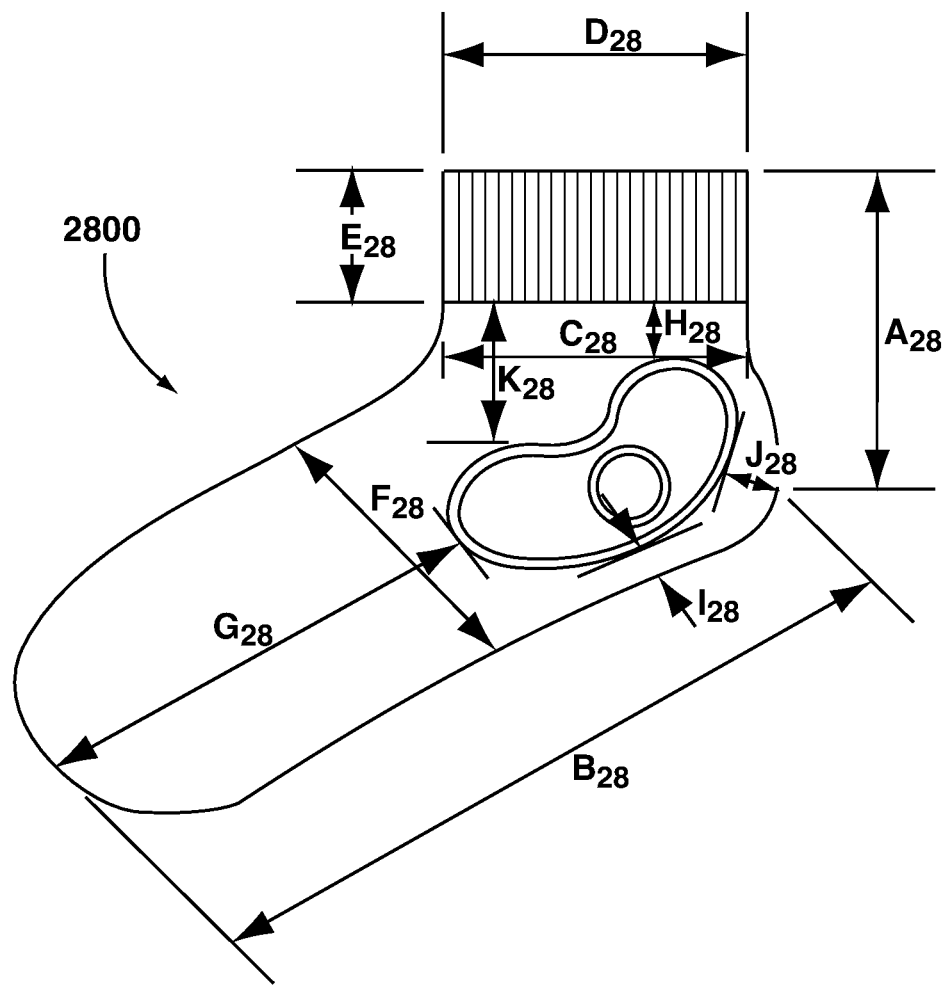
FIG. 28A is a schematic side view of an exemplary running sock according to an aspect of the present invention, showing various dimensions thereof.
Figure 29A:
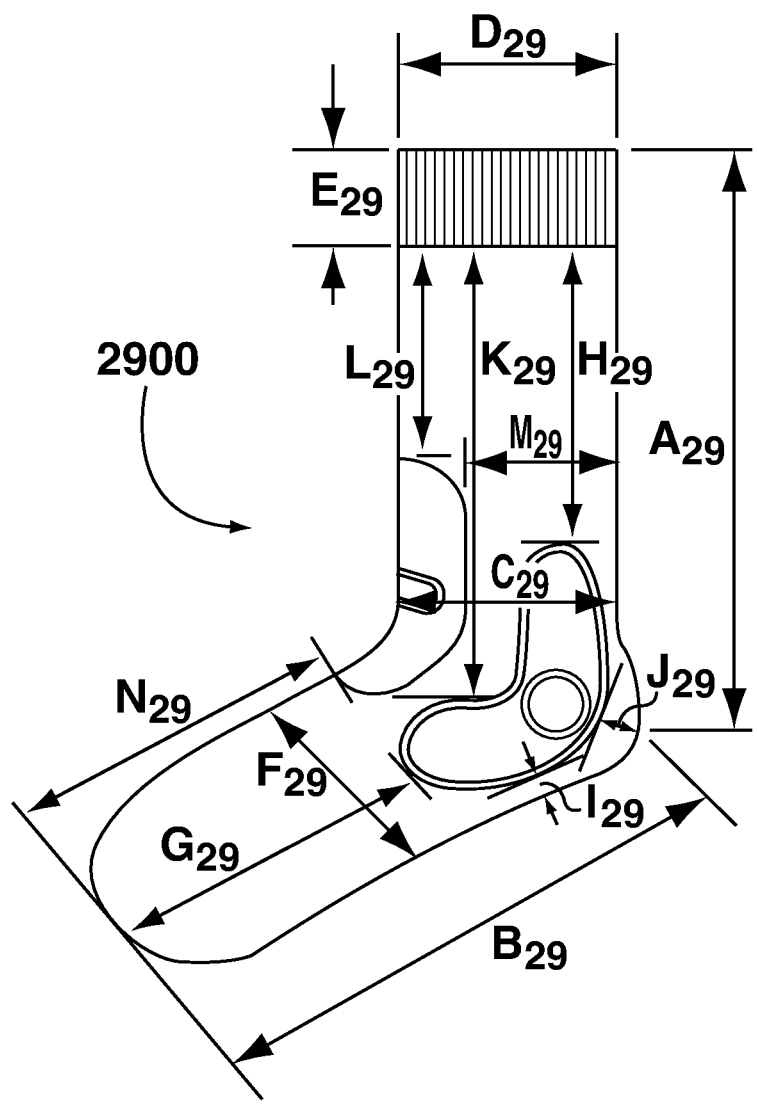
FIG. 29A is a schematic side view of an exemplary hockey sock according to an aspect of the present invention, showing various dimensions thereof.
Figure 30A:
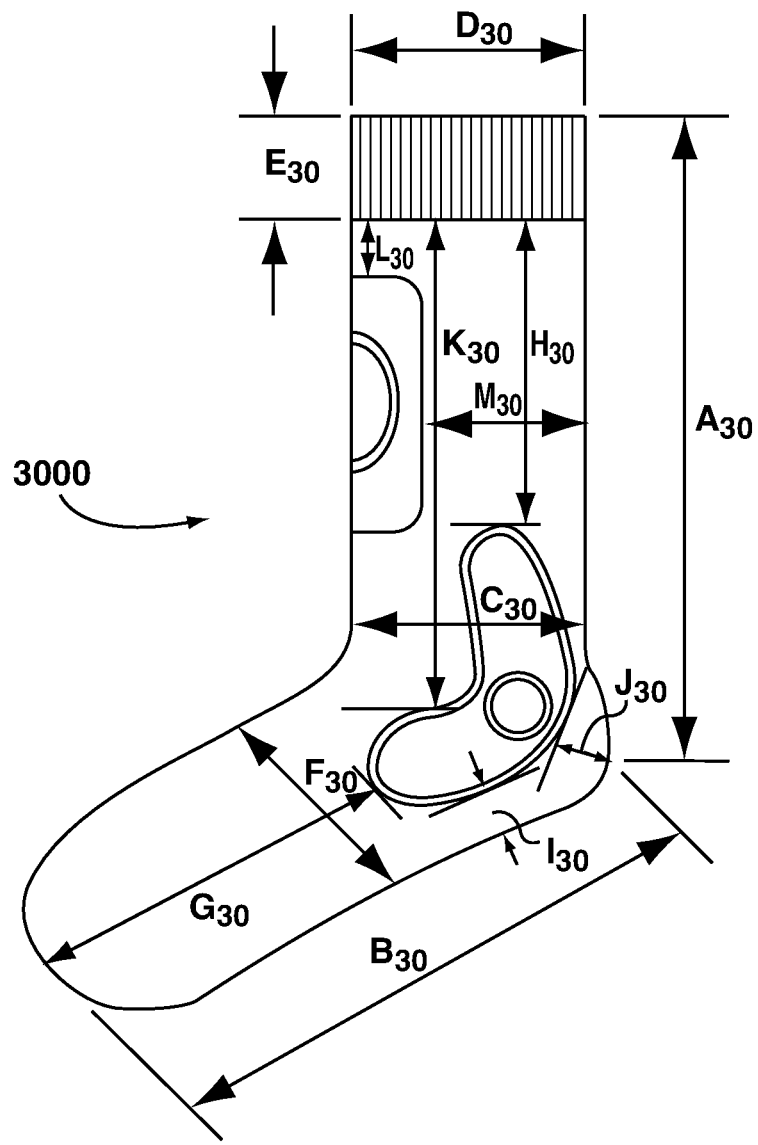
FIG. 30A is a schematic side view of an exemplary skiing sock according to an aspect of the present invention, showing various dimensions thereof.

FIGS. 28A, 29A and 30A show schematic representations of exemplary stabilizing socks 2800, 2900A, 2900B, 3000 in which the stabilizer regions take the form of pockets, according to aspects of the present invention. FIGS. 28A, 29A and 30A show dimensions for the stabilizing socks 2800, 2900, 3000 themselves as well as for the positioning of the pockets. Stabilizing socks according to aspects of the present invention will generally be made from a resilient, elastic fabric, and therefore FIGS. 28A, 29A and 30A show the exemplary socks in a flattened, unstretched condition to permit various dimensions to be illustrated. In a currently preferred embodiment, the relative positions of the medial and lateral pockets are the same for both the left side sock and the right side sock. Moreover, although in FIGS. 28A, 29A and 30A only one side of the sock is illustrated, because FIGS. 28A, 29A and 30A are schematic representations that are not to scale, these figures are representative of both the medial and lateral sides. In particular, the socks shown in FIGS. 28A, 29A and 30A are equally representative of both a medial side of a right foot sock and a lateral side of a left foot sock, notwithstanding the differential placement of the medial and lateral pockets. Accordingly, the associated tables 2812 in FIGS. 28B, 29B and 30C provide dimensions for both the medial and lateral sides.

In a presently preferred embodiment, the foot stabilizer socks are provided in medium (M), large (L) and extra-large (XL) sizes, and the pockets for the medial and lateral stabilizer pads, boot bang protector pads and lace bite protector pads are provided in a medium (M) size for "medium" pads, and a large/extra-large (L/XL) size for "large" and "extra-large" pads, with each size of pocket being able to accommodate the three different thicknesses of the respective pads. The medium (M) pockets are used with the medium (M) socks and the large/extra-large (L/XL) pockets are used with the large (L) and extra-large (XL) socks.

Figures 31A, 31B:
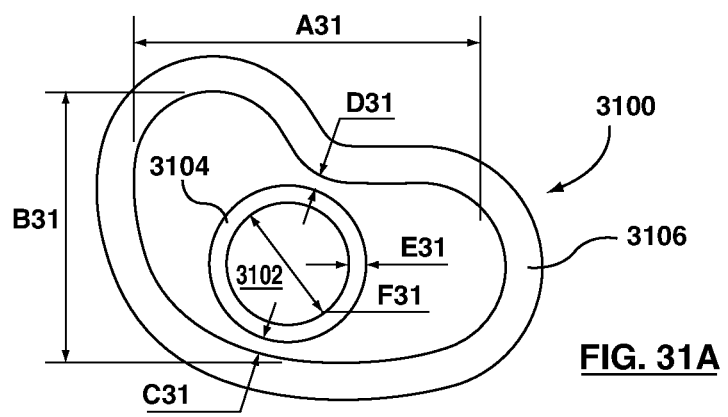
FIG. 31A is a schematic view of an exemplary stabilizer pad pocket for a running socks according to an aspect of the present invention, showing various dimensions thereof.
FIG. 31B shows a table containing exemplary dimensions of the stabilizer pad pocket of FIG. 31A.

FIG. 31A shows an exemplary pocket 3100 for a stabilizer pad of the type shown in FIGS. 9C and 9D, such as the stabilizer pad 2400. The pocket 3100 may be used for either a medial stabilizer pad or a lateral stabilizer pad. The pocket 3100 includes an aperture 3102 surrounded by a reinforced border region 3104 and a peripheral attachment region 3106 which is secured to a stabilizer sock, such as by stitching, adhesive, or other suitable techniques. A pad may be inserted into the pocket 3100 through the aperture 3102. The reinforced border region 3104 may be formed by stitching, application of a rubber or similar coating, or the like, and the peripheral attachment region 3106 may be similarly reinforced. Exemplary dimensions for each size of pocket 3100 are shown in the table 3108 in FIG. 31B.

Figures 32A, 32B:
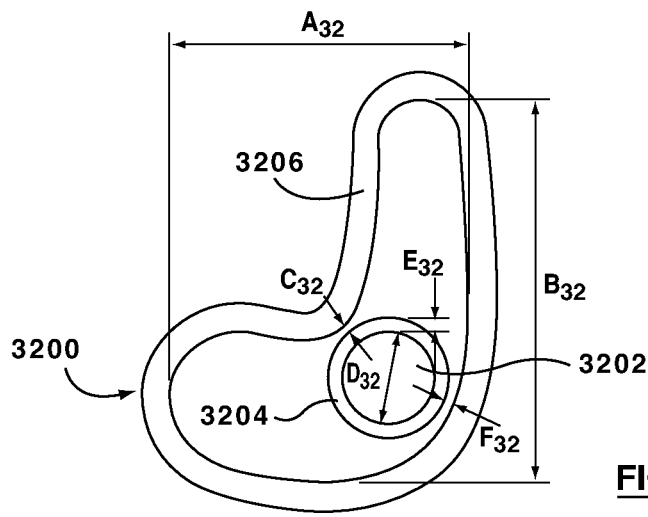
FIG. 32A is a schematic view of an exemplary stabilizer pad pocket for hockey and skiing socks according to an aspect of the present invention, showing various dimensions thereof.
FIG. 32B shows a table containing exemplary dimensions of the stabilizer pad pocket of FIG. 32A.

Similarly to FIG. 31A, FIG. 32A shows an exemplary pocket 3200 for a stabilizer pad of the type shown in FIGS. 16A and 16B, such as the stabilizer pad 2300, which pocket 3200 includes an aperture 3202 for inserting a pad, a reinforced border region 3104 surrounding the aperture 3202 and a peripheral attachment region 3206 for securing the pocket 3200 to a stabilizer sock. The table 3208 in FIG. 32B provides exemplary dimensions for each size of pocket 3200.

Figures 33A, 33B:
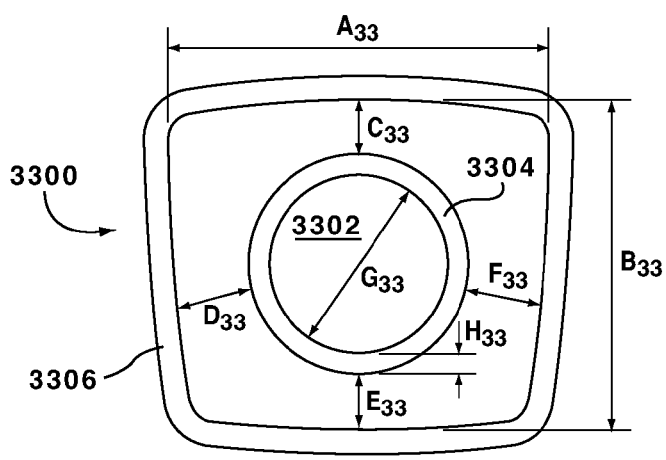
FIG. 33A is a schematic view of an exemplary boot bang protector pad pocket for skiing socks according to an aspect of the present invention, showing various dimensions thereof.
FIG. 33B shows a table containing exemplary dimensions of the boot bang protector pad pocket of FIG. 33A.
Figures 34A, 34B:
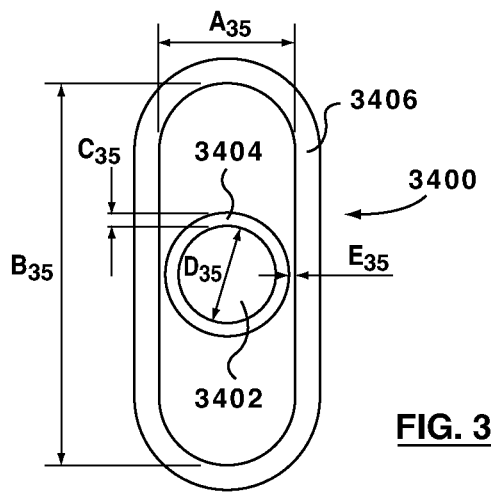
FIG. 34A is a schematic view of an exemplary lace bite protector pad pocket for hockey socks according to an aspect of the present invention, showing various dimensions thereof.
FIG. 34B shows a table containing exemplary dimensions of the lace bite protector pad pocket of FIG. 34A.

FIG. 33A shows an exemplary pocket 3300 for boot bang protector pads, such as the boot bang protector pads 2500, 2600, which includes an aperture 3302 surrounded by a reinforced border region 3304 and a peripheral attachment region 3306. FIG. 34A similarly shows an exemplary pocket 3400 for a lace bite protector pad, such as the lace bite protector pad 2700. The pocket 3400 includes an aperture 3402, a reinforced border region 3304 around the aperture 3302 and a peripheral attachment region 3406 for securing the pocket 3400 to a stabilizer sock. The table 3308 in FIG. 33B shows exemplary dimensions for the pocket 3300 shown in FIG. 33A, and the table 3408 in FIG. 34B shows exemplary dimensions for the pocket 3400 shown in FIG. 34A.

Various embodiments of aspects of the present invention have been described by way of example. It will be apparent to persons skilled in the art that a number of variations and modifications can be made without departing from the scope of the invention as defined in the claims.

What is claimed is:

1. A sock system comprising:
a sock, the sock having a foot section, wherein:
the foot section has a shape corresponding to a human foot and comprises:
a rearfoot portion corresponding to human calcaneous and talus bones and to tibial and fibular malleoli;
a forefoot portion corresponding to human metatarsal and phalanx bones; and
a midfoot portion between the rearfoot portion and the forefoot portion and corresponding to human cuboid, navicular and cuneiform bones;
the sock has a medial stabilizer region on a medial side of the sock corresponding to a medial side of the foot and a lateral stabilizer region on a lateral side of the sock corresponding to a lateral side of the foot;
the medial stabilizer region and the lateral stabilizer region are separate and distinct from one another;
the medial stabilizer region covers a forward medial region of the rearfoot portion and a rearward medial region of the midfoot portion;
the lateral stabilizer region covers a forward lateral region of the rearfoot portion;
the medial stabilizer region:
starts at a position on the rearfoot portion corresponding to a position on the foot posterior to the tibial malleolus;
extends inferiorly of and anteriorly relative to an area on the rearfoot portion corresponding to the tibial malleolus; and
ends at a position on the midfoot portion corresponding to a position on the foot anterior to the tibial malleolus;
the medial stabilizer region includes a medial malleolal concavity at its upper edge to accommodate the tibial malleolus;

the lateral stabilizer region:
  starts at a position on the rearfoot portion corresponding to a position on the foot posterior to the fibular malleolus;
  extends inferiorly of and anteriorly relative to an area on the rearfoot portion corresponding to the fibular malleolus; and
  ends at a position corresponding to a position on the foot anterior to the fibular malleolus;
the lateral stabilizer region includes a lateral malleolal concavity at its upper edge to accommodate the fibular malleolus;
wherein each of the medial stabilizer region and the lateral stabilizer region consists of a pocket for receiving, respectively, a stabilizer pad;
the sock system further comprising:
  a plurality of stabilizer pads shaped to fit the pockets;
  wherein the plurality of stabilizer pads includes stabilizer pads having different thicknesses;
wherein each pocket includes a respective aperture through which one of the plurality of stabilizer pads is insertable into, and removable from, the respective pocket; and
the pockets and their respective apertures and also the plurality of stabilizer pads are adapted so that appropriate perimeter sizes of the pockets and of the plurality of stabilizer pads are selected for a size of the human foot with which the plurality of stabilizer pads are used.

2. The sock system of claim 1, wherein:
the medial stabilizer region extends from a position on the rearfoot portion corresponding to a position on the foot posterior to the tibial malleolus and anterior to an Achilles tendon, across a part of the rearfoot portion corresponding to a lower medial part of the talus and an upper medial part of the calcaneous to terminate at a position on the midfoot portion corresponding to the navicular bone; and
the lateral stabilizer region extends from a position on the rearfoot portion corresponding to a position on the foot posterior to the fibular malleolus and anterior to the Achilles tendon, across a lower part of the rearfoot portion corresponding to a lower lateral part of the talus and an upper lateral part of the calcaneous.

3. The sock system of claim 1, wherein the lateral stabilizer region extends to and terminates at a position on the rearfoot portion corresponding to a position on the foot posterior and proximal to the cuboid bone.

4. The sock system of claim 1, wherein the plurality of stabilizer pads comprises both a plurality of medial stabilizer pads, each corresponding in perimeter size and shape to the medial stabilizer region and also a plurality of lateral stabilizer pads, each corresponding in size and shape to the lateral stabilizer region.

* * * * *